(12) United States Patent
Zetter et al.

(10) Patent No.: US 7,993,863 B2
(45) Date of Patent: Aug. 9, 2011

(54) METHODS FOR DIAGNOSIS AND PROGNOSIS OF CANCER

(75) Inventors: Bruce R. Zetter, Wayland, MA (US); Lere Bao, Newton, MA (US); Jacqueline Banyard, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 395 days.

(21) Appl. No.: 10/508,440

(22) PCT Filed: Mar. 18, 2003

(86) PCT No.: PCT/US03/08100
§ 371 (c)(1),
(2), (4) Date: Sep. 14, 2005

(87) PCT Pub. No.: WO03/079884
PCT Pub. Date: Oct. 2, 2003

(65) Prior Publication Data
US 2006/0078882 A1    Apr. 13, 2006

Related U.S. Application Data

(60) Provisional application No. 60/365,667, filed on Mar. 19, 2002.

(51) Int. Cl.
*G01N 33/574* (2006.01)
(52) U.S. Cl. ..................... 435/7.23; 530/350
(58) Field of Classification Search ................ None
See application file for complete search history.

(56) References Cited

U.S. PATENT DOCUMENTS

2003/0224982 A1* 12/2003 Li et al. .............. 514/12
2004/0250304 A1* 12/2004 Iwatsubo et al. ........... 800/12

FOREIGN PATENT DOCUMENTS

WO    WO 00/58473 A2    10/2000
WO    01/58943    *   8/2001

OTHER PUBLICATIONS

Skolnick et al. (Trends in Biotech., 18(1):34-39, 2000).*
Tockman et al, Cancer Research vol. 52 p. 2711s (1992).*
Blood CH, Zetter BR, Tumor interactions with the vasculature: angiogenesis and tumor metastasis, *Biochim Biophys Acta.* 1990;1032(1):89-118.
Fidler IJ, Gersten DM, Hart IR, The biology of cancer invasion and metastasis, *Adv Cancer Res*1978;28:149-250.
Fidler IJ, Rationale and methods for the use of nude mice to study the biology and therapy of human cancer metastasis, *Cancer Metastasis Rev.* 1986;5(1):29-49.
Haemmerli G, Sträuli P, in vitro motility of cells from human epidermoid carcinomas. A study by phase-contrast and reflection-contrast cinematography, *Int J Cancer.* 1981;27(5):603-10.
Hosaka S, Suzuki M, Goto M, Sato H, Motility of rat ascites hepatoma cells, with reference to malignant characteristics in cancer metastasis, Gann. Apr. 1978;69(2):273-6.
Liotta LA, Stracke ML, Tumor invasion and metastases: biochemical mechanisms, *Cancer Treat Res.* 1988;40:223-38.
Nicolson GL, Cancer metastasis: tumor cell and host organ properties important in metastasis to specific secondary sites, *Biochim Biophys Acta.* 1988;948(2):175-224.
Zetter BR, The cellular basis of site-specific tumor metastasis, N Engl J Med. 1990;322(9):605-12.
International Search Report for PCT/US03/08100 mailed on Oct. 20, 2003.
Breslin, P.W. et al. Characterization of deletions in a new human collagen-like gene. American Journal of Human Genetics. Oct. 24-28, 1995, vol. 57, No. 4 SUPPL., p. A141, Abstract No. 796.
Banyard et al., Collagen XXIII expression is associated with prostate cancer recurrence and distant metastases. Clin Cancer Res. May 1, 2007;13(9):2634-42.
Banyard et al., Type XXIII collagen, a new transmembrane collagen identified in metastatic tumor cells. J Biol Chem. Jun 6, 2003;278(23):20989-94. Epub Mar 18, 2003.
Gordon et al., Cloning of a new collagen, type XXIII, expressed in cornea. IOVS. Mar. 15, 2000;41(4): Abst 3997.

* cited by examiner

*Primary Examiner* — Sheela J Huff
(74) *Attorney, Agent, or Firm* — Wolf, Greenfield & Sacks, P.C.

(57) ABSTRACT

We have discovered a protein in humans, herein referred to as collagen like gene (CLG) product (SEQ ID NOS: 12 and 13), that is expressed in human prostate cancer and breast cancer cell lines but not in normal adult, placenta, lung, liver, skeletal muscle, kidney or pancreas tissues. We have also discovered that the level of CLG mRNA expression correlates positively with the metastatic potential of the cancer cell lines tested.

20 Claims, 12 Drawing Sheets

```
Homo sapiens alpha 1 type XXIII collagen (COL23A1) mRNA
SOURCE         heart FEATURES             Location/Qualifiers
    source           1..3202
                     /organism="Homo sapiens"
                     /chromosome="5"
                     /map="5q35"
    SEQ              1..3202
                     /gene="COL23A1"
    5'UTR            1..358
    CDS              359..2113
                     /product="alpha 1 type XXIII collagen"
    misc_feature     1133..1270
                     /exon splice variant ORIGIN
     1 agaggtgcgc gctgcgcgtg ggatcagccc ggcgccgacg ggtggctccg aggagctcgc
    61 tccttcctcg ccccgcccc ctcgccgcgc ggggccagcc cggccgctcc tccctgggt
   121 gggtccctgc tccttttctg gcagggtcta tttgcataga ggaaactgcc caaagtggcc
   181 gctgtggagg agctggctgc ggcgaagggg gcgtgcgcgg cgatccgctg ctacccggag
   241 gctaaccccc gcgcccggcg gacctcgtgc ctcgggctgt cccgcctgct cctctcgcac
   301 ccagcctctg ccccagcagc accgcccct cggagagtcc acgcgcgacg aacgcgccat
   361 gggcccaggc gagcgcgccg gtggcggcgg cgacgcgggg aagggcaatg cggcgggcgg
   421 cggcggcgga gggcgctcgg cgacgacggc cgggtcccgg gcggtgagcg cgctgtgcct
   481 gctgctctcc gtgggctcgg cggctgcctg cctgctgctg ggtgtccagg cggccgcgct
   541 gcagggccgg gtggcggcgc tcgaggagga gcgggagctg ctcggcgcg cggggccgcc
   601 aggcgccctg gacgcctggg ccgagccgca cctggagcgc ctgctgcggg agaagttgga
   661 cggactagcg aagatccgga ctgctcggga agctccatcc gaatgtgtct gccccccagg
   721 gcccctgga cggcgcggca agcctgggag aagaggcgac cctggtcctc cagggcaatc
   781 aggacgagat ggctacccgg gacccctggg tttggatggc aagcccggac ttccaggccc
   841 gaaaggggaa aagggtgcac caggagactt tggccccgg ggagaccaag gacaagatgg
   901 agctgctggg cctccggggc cccctggacc tcctgggcc cggggccctc ccgacactgg
   961 gaaagatggc cccaggggag cacaaggccc agcgggcccc aaggagagc ccggacaaga
  1021 cggcgagatg ggcccaaagg gaccccagg gccaagggt gagcctggag tacctggaaa
  1081 gaagggcgac gatgggacac caagccagcc tggaccacca gggcccaagg gggcctcact
  1141 ctctgccctg tccccaagcc aggaactggg tgtcatcctc atgccttgct cccccaaccc
  1201 ctcgcaacgc caccaaatcc tggccaggca gtctccaaaa tgtcccttga gccctggct
  1261 gccccaaggc gagccaggga gcatggggcc tcggggagag aacggtgtgg acggtgcccc
  1321 aggaccgaag ggggagcctg gccaccgagg cacggatgga gctgcagggc cccggggtgc
  1381 cccaggcctc aagggcgagc agggagacac agtggtgatc gactatgatg gcaggatctt
  1441 ggatgccctc aaggggcctc ccggaccaca ggggccccca gggccaccag gatccctgg
  1501 agccaagggc gagcttggat gcccggtgc cccaggaatc gatggagaga agggccccaa
  1561 aggacagaaa ggagacccag gagagcctgg ccagcagga ctcaaagggg aagcaggcga
  1621 gatgggcttg tccggcctcc cgggcgctga cggcctcaag ggggagaagg gggagtcggc
  1681 gtctgacagc ctacaggaga gcctggctca gctcatagtg gagccagggc ccctggccc
  1741 ccctggcccc ccaggcccga tgggcctcca gggaatccag ggtcccaagg gcttggatgg
  1801 agcaaaggga gagaagggtg cgtcgggtga gagaggcccc agcggcctgc ctgggccagt
  1861 tggcccaccg ggccttattg ggctgccagg aaccaaagga gagaagggca gacccgggga
  1921 gccaggacta gatggttttc ctggaccccg aggagagaaa ggtgatcgga gcgagcgtgg
  1981 agagaaggga gaacgagggg tccccggccg gaaaggagtg aagggccaga agggcgagcc
  2041 gggaccacca ggcctggacc agccgtgtcc cgtgggcccc gacgggctgc ctgtgcctgg
  2101 ctgctggcat aagtgaccca caggcccagc tcacacctgt acagatccgt gtggacattt
  2161 ttaattttg taaaaacaaa acagtaatat attgatcttt tttcatggaa tgcgctacct
  2221 gtggcctttt aacattcaag agtatgccca cccagcccca aagccaccgg catgtgaagc
  2281 tgccggaaag tggacaggcc agaccaggga gatgtgtacc tgaggggcac ccttgggcct
  2341 gggctttccc aggaaggaga tgaaggtaga agcacctggc tcgggcaagg ctagaaagat
  2401 gctacgttgg gccttcagtc acctgatcag cagagagact ctcagctgtg gtactgccct
  2461 gtaagaacct gcccccgcaa aactctggag tccctgggac acaccctatc caagaagacc
```

FIGURE 1A

```
2521  caggggtgga  acagcggctg  ctgttgctcc  tggcctcatc  agcctccaaa  ctcaaccaca
2581  accagctgcc  tctgcagttg  gacaagactt  ggcccccgga  caagactcgc  ccagcacttg
2641  cggctgggcc  cggggagcag  tgagtggaaa  tcccccacga  gggtctagct  ctaccacatt
2701  caggaggcct  caggaggcca  gcctgccatg  agagcacatg  tcctctggcc  aggagtagtg
2761  gctgagctct  gtgatcgctg  tgatgtggac  ccagctccag  ggagcagagt  gtcggggatg
2821  gaggggccca  gcctggactg  actgtacttc  ctgtctctgt  ttccattatc  acccagagag
2881  ggacaagata  ggacatggcc  tggaccaggg  aggcaggcct  cccactcaga  gtctgggtct
2941  cactggcccc  aagtctccca  cccagaactc  tggccaaaaa  tggctctcta  ggtgggctgt
3001  gcaggcaaag  caaagctcag  ggctggttcc  cagctggcct  gagcaggggg  cctgccacca
3061  gacccaccca  cgctctgacg  agaggctttt  ccacctccag  caagtgttcc  cagcaaccag
3121  ctccatcctg  gctgcttgcc  ttccatttcc  gtgtagatgg  agatcactgt  gtgtaataaa
3181  ccacaagtgc  gtgtcaaaaa  aa
```

Homo sapiens alpha 1 type XXIII collagen (COL23A1) Translation
SQ   SEQUENCE   585 AA
exon splice underlined

```
MGPGERAGGG  GDAGKGNAAG  GGGGGRSATT  AGSRAVSALC  LLLSVGSAAA  CLLLGVQAAA
LQGRVAALEE  ERELLRRAGP  PGALDAWAEP  HLERLLREKL  DGLAKIRTAR  EAPSECVCPP
GPPGRRGKPG  RRGDPGPPGQ  SGRDGYPGPL  GLDGKPGLPG  PKGEKGAPGD  FGPRGDQGQD
GAAGPPGPPG  PPGARGPPDT  GKDGPRGAQG  PAGPKGEPGQ  DGEMGPKGPP  GPKGEPGVPG
KKGDDGTPSQ  PGPPGPKGAS  LSALSPSQEL  GVILMPCSPN  PSQRHQILAR  QSPKCPLSPW
LPQGEPGSMG  PRGENGVDGA  PGPKGEPGHR  GTDGAAGPRG  APGLKGEQGD  TVVIDYDGRI
LDALKGPPGP  QGPPGPPGIP  GAKGELGLPG  APGIDGEKGP  KGQKGDPGEP  GPAGLKGEAG
EMGLSGLPGA  DGLKGEKGES  ASDSLQESLA  QLIVEPGPPG  PPGPPGPMGL  QGIQGPKGLD
GAKGEKGASG  ERGPSGLPGP  VGPPGLIGLP  GTKGEKGRPG  EPGLDGFPGP  RGEKGDRSER
GEKGERGVPG  RKGVKGQKGE  PGPPGLDQPC  PVGPDGLPVP  GCWHK
```

FIGURE 1B

```
LOCUS       AY158896                2733 bp    mRNA    linear   ROD 07-JAN-2003
DEFINITION  Rattus norvegicus alpha 1 type XXIII collagen (Col23a1) mRNA,
            complete cds.
ACCESSION   AY158896
VERSION     AY158896
KEYWORDS
SOURCE      Rattus norvegicus (Norway rat)
  ORGANISM  Rattus norvegicus
            Eukaryota; Metazoa; Chordata; Craniata; Vertebrata; Euteleostomi;
            Mammalia; Eutheria; Rodentia; Sciurognathi; Muridae; Murinae;
            Rattus.
REFERENCE   1  (bases 1 to 2733)
  AUTHORS   Banyard,J., Bao,L. and Zetter,B.R.
  TITLE     Type XXIII collagen: a new transmembrane collagen upregulated in
            metastatic tumor cells
  JOURNAL   Unpublished
REFERENCE   2  (bases 1 to 2733)
  AUTHORS   Banyard,J., Bao,L. and Zetter,B.R.
  TITLE     Direct Submission
  JOURNAL   Submitted (04-OCT-2002) Department of Surgery, Children's Hospital,
            300 Longwood Ave., Boston, MA 02115, USA
FEATURES             Location/Qualifiers
     source          1..2733
                     /organism="Rattus norvegicus"
                     /strain="Copenhagen"
                     /db_xref="taxon:10116"
                     /cell_line="AT6.1"
                     /cell_type="Dunning R-3327 prostate adenocarcinoma"
     gene            1..2733
                     /gene="Col23a1"
     CDS             129..1727
                     /gene="Col23a1"
                     /codon_start=1
                     /product="alpha 1 type XXIII collagen"
                     /protein_id="AAO18362"
                     /translation="MGAGERAAGGGGTQDPGAGCGARALGALCLLLSVGSATACLLLG
                     AQAAALHGRVAALEQERELLRRAGPSGALAAWAETHLERLLREKLDGVAKLRTVREAP
                     SECICPPGPPGRRGKPGRRGDPGPPGQSGRDGYPGPLGLDGKPGLPGPKGEKGAPGDF
                     GPRGAQGQDGAAGPPGPPGPPGARGPPGDTGKDGPRGAQGPEGPRGESGQDGEMGPMG
                     PPGPKGEPGTPGKKGDDGIPSQPGLPGPPGPKGEPGDVGPQGETGVDGAPGLKGEPGH
                     PGTDGAIGPRGPPGLKGEQGDTVVIDYDGRILDALKGPPGPQGAPGPPGIPGAKGELG
                     LPGAPGIDGEKGPKGPKGDPGEPGPAGPKGETGEMGLSGLPGADGPKGEKGESASDHL
                     QESLAQIIVEPGPPGPPGPPGPMGLQGIQGPKGLDGAKGEKGASGERGPHGLPGPVGP
                     PGLIGLPGTKGEKGRPGEPGLDGFPGPRGEKGDRSERGEKGERGVPGRKGVKGQKGEP
                     GPPGLDQPCPVGPDGLPVPGCWHK"
BASE COUNT      598 a    808 c    904 g    423 t
ORIGIN
        1 ggccgctgcg tctgagcggg cggctagggg ggcgtgcgcg atccacggcc gcccggacgc
       61 cgagcccgc agccgccgac ctggagccac cccgggccgc agcgcctacg cagagccggc
      121 cggtcgccat gggcgcgggc gagcgcgcgg cgggcggggg aggcacgcag gaccccggcg
      181 cgggctgcgg ggcgcgggcg ctgggcgcgc tgtgcctgct gctgtcggtg ggctctgcga
      241 ccgcctgtct cctgctgggc gcccaagcgg ccgccttgca tggccgagtg gcggcgctgg
      301 agcaggagcg cgaactgttg cggcgtgcgg ggcgtccgg agccctggcg gcctgggccg
      361 aaacgcacct ggagcgcctg ctacgggaga agttggatgg agtcgccaag ctcaggacag
      421 ttcgagaagc ccctctgag tgcatctgtc ccctggtcc cctggacgg cgtggcaagc
      481 cgggacgaag aggcgaccca ggccctccgg ggcaatccag acgagatggc tacccgggac
      541 ctctaggtct ggacggcaag ccaggacttc caggcccaa aggggaaaag ggtgcaccag
      601 gagactttgg cccacgggga gccaagggc aagatggagc tgcaggacca cctgggcctc
      661 ctgggccacc tgggcccgg ggcctcctg gtgacactgg aaagatggt ccccgaggag
      721 ctcaaggccc agagggtccc agaggagagt ctggacaaga tggcgaaatg ggcccatgg
      781 gacctccagg acccaaggga gaacctgca ctcctggaaa gaggggat gatgggatac
      841 ccagccagcc aggactccct ggaccccag ggcccaaggg tgagccagga gatgtggggc
```

FIGURE 2A

```
 901 cccaaggaga gactggagta gacggtgccc ctggactgaa ggggagccc ggtcacccag
 961 gcacggatgg agccataggg ccccggggtc ccccgggcct caagggagaa caaggtgaca
1021 cggtggtaat cgactatgat ggcaggatct tagatgccct gaagggtcct cccggaccac
1081 agggagctcc tgggccacca gggatccctg gagccaaggg tgaacttgga ttgcctggtg
1141 ctccaggaat cgatggagag aagggtccca aaggaccaaa aggagaccca ggagagcctg
1201 gaccagctgg acccaaaggg gaaacaggag agatgggcct gtcaggtctt ccgggtgccg
1261 atggtcccaa gggagaaaag ggagagtcag catctgacca tctacaggag agcctggccc
1321 agatcatagt ggagccaggg ccccccggtc ctcctgggcc ccccggcccc atgggccttc
1381 aggggatcca gggtcccaag ggcctggatg gagccaaggg agaaaagggt gcatcgggtg
1441 agagaggccc tcacggtctg cctggaccag ttggcccacc aggccttatt gggttgcccg
1501 gaaccaaagg agagaagggc cgacccggag agccaggact cgacggtttc cctggaccca
1561 ggggagagaa aggcgaccga agtgaacgag gagagaaggg ggagcgagga gttcctggtc
1621 ggaaaggagt gaaaggccag aagggagagc caggcccacc aggccttgac cagccatgcc
1681 ctgtgggccc cgacggggttg cctgtgcctg gttgctggca taagtgatcc tcgggcatag
1741 cccccaacct gtacagatcc gtttggatgt tttaactcg tgtaaaaaca aaacagtaat
1801 atattgaact tctttatggg atgcgccaac tgtgtggcct tgtaagattt gcaagtgtgc
1861 caaccagccc ctggaccatc tgcacaggaa gcggcagga acgcagacag gctggctgct
1921 ctggggaaac ttgtgttcga aggcccccgg cagggcctgg ctttcccagg gagaggacga
1981 gggtgaaaac gcctggctca ggtgaggatg gacagactcc agtcgggct tacaatcacc
2041 tgattagcag agacttacaa caactgtcct ctgaaacccc actgcccaa cttctcactg
2101 tccaacgaca ccccttgga cacctgctgt accctcttgc ttctggactg tgccacaggc
2161 agctgcactg ggaccctagg tttaacaggg caggcgaaga ttcctagagt ccagcacttg
2221 gggagaaggc aatggaagaa cccaagaggg ccttgctcca cccagttcag taggcttcct
2281 gacacaggag cttgtaccct cttcagacct tgggaaatgg caagactctg tggatacctc
2341 actggcaggc agcccagtga accctgactg tagggtgaag aggccatacc cactagttgg
2401 tacttcctgt ctcctcaccc agagcaggaa caggaagtgg ctttgtcagc ccaaggagac
2461 aggcctcctg ttcagaactt gtatctcact ggccccaagt ctctgaccta gacctctggt
2521 tagcctgaca gaaacaggcc cctagtaaa tgaccctgaa ggctggtccc ccggcaagcc
2581 tgagcaaagc acctgtgact gaaacccctg ccctctctgg agaggcttga acacctataa
2641 cgaagtttcc tagctcctgc tccatcacgg cctcacatcc ctctgcatat aaaggcacca
2701 tgagcaataa accacaaatg tgcgtccagt aaa
```

FIGURE 2B

DEFINITION: Mouse CLG Sequence

```
    misc_feature    3..1457
                    =" incomplete ORF, missing 5'end with translation start codon"
    misc_feature    1458..1460
                    ="stop codon"
    misc_feature    1458..2024
                    ="3'UTR"

ORIGIN
       1 cggccgccct gcatggccga gtggcggcgc tggagcagga gcgcgagctg ttgcggcatg
      61 cggggccgtc cggagccctg gccgcctggg ccgaaacgca cctggagcgc ctgttacggg
     121 agaagttgga tggagtcgcc aagctcagga cagttcgaga agccccatct gagtgcatct
     181 gtcccctgg tccccctgga cggcgtggca agcctggacg aagaggcgac cctggtcctc
     241 cagggcaatc aggacgagat ggctaccggg acctctaggg tctggacggc aagcccggac
     301 ttccaggccc caaaggggaa aaggtgcac caggagactt tggcccacgg ggagcccaag
     361 ggcaagatgg agctgcagga ccacctgggc ctcctgggcc acctggggcc cggggccctc
     421 ctggtgacac tgggaaagat ggtccccgag gagctcaagg cccagagggt cccagaggag
     481 agtctggaca agatggcgaa atgggcccca tgggacctcc aggacccaag ggagaacctg
     541 gcactcctgg aaagaagggg gatgatggga tacccagcca gccaggactc cctggacccc
     601 cagggcccaa gggtgagcca ggagatgtgg ggccccaagg agagactgga gtagacggtg
     661 ccctggact gaaggggag cccggtcacc caggcacgga tggagccata gggccccggg
     721 gtccccgggg cctcaaggga gaacaaggtg acacggtggt aatcgactat gatggcagga
     781 tcttagatgc cctgaagggt cctcccggac cacagggagc tcctgggcca ccagggatcc
     841 ctggagccaa gggtgaactt ggattgcctg gtgctccagg aatcgatgga gagaagggtc
     901 ccaaaggacc aaaaggagac ccaggagagc ctggcccaaa ggggaaacag
     961 gagagatggg cctgtcaggt cttccgggtg ccgatggtcc caaggagaa aagggagagt
    1021 cagcttctga ccatctacag gagagcctgg cccagatcat agtggagcca gggcccccg
    1081 gtcctcctgg gccccccggc cccatgggcc ttcaggggat ccaggtccc aagggcctgg
    1141 atggagccaa gggagaaaag ggtacatcgg gtgagagagg ccctcacggc ctgcctggac
    1201 cagttggccc accaggcctt attggggttgc caggaaccaa aggagagaag ggcagacctg
    1261 gagaaccagg actcgatggg ttccctggac caggggagac gaaggggtgac cgaagtgaac
    1321 gtggagagaa ggggggagcga ggagttcctg gccggaaagg cgtgaagggc cagaagggag
    1381 agccgggccc accaggcctt gaccagccat gtcctgtggg ccccgatggg ttgcctgtgc
    1441 ctggttgctg gcataagtga tcctcagaca taaccccctga cctgtacaga tccgtttgga
    1501 tgttttgaac tcatgtaaaa acaaaacagt aatatattga acttctttat gggatgcgcc
    1561 aactgtggcc atgtaacatt tgcaagtgtg ccaaccagcc cctggacaat ctgcacagga
    1621 agccagcagg aatgcggaca ggctgctctg aggaaacttc tgttcaaagg ccctgggtag
    1681 ggcctggctt tccagggaa gatgacgagg gtgaaaacgc ctggctcagg tgaggctgga
    1741 cagactccag gttgggctca taatcacctg attagcagag acttgcaaca aactgtttcc
    1801 tgaaacccca ttgcccagtt ctcactgtcc aatagcaccc ccttggacaa cttgcttgta
    1861 gccttcttgc ttcgcggact gtgcccgtag gcagttgcac tggggccct atgtttccac
    1921 aggggcccag caaagattct taaagtccag cacttggggg agaagggcct ggggagaacc
    1981 ccgagaggcc ttggtccccc aatttaagcc cttccaaacc accg
```

FIGURE 3A

Translation of mouse CLG Sequence:  485AA
(incomplete ORF, missing 5'end with translation start codon)

```
AALHGRVAAL  EQERELLRHA  GPSGALAAWA  ETHLERLLRE  KLDGVAKLRT  VREAPSECIC
PPGPPGRRGK  PGRRGDPGPP  GQSGRDGYPG  PLGLDGKPGL  PGPKGEKGAP  GDFGPRGAQG
QDGAAGPPGP  PGPPGARGPP  GDTGKDGPRG  AQGPEGPRGE  SGQDGEMGPM  GPPGPKGEPG
TPGKKGDDGI  PSQPGLPGPP  GPKGEPGDVG  PQGETGVDGA  PGLKGEPGHP  GTDGAIGPRG
PPGLKGEQGD  TVVIDYDGRI  LDALKGPPGP  QGAPGPPGIP  GAKGELGLPG  APGIDGEKGP
KGPKGDPGEP  GPAGPKGETG  EMGLSGLPGA  DGPKGEKGES  ASDHLQESLA  QIIVEPGPPG
PPGPPGPMGL  QGIQGPKGLD  GAKGEKGTSG  ERGPHGLPGP  VGPPGLIGLP  GTKGEKGRPG
EPGLDGFPGP  RGEKGDRSER  GEKGERGVPG  RKGVKGQKGE  PGPPGLDQPC  PVGPDGLPVP
GCWHK
```

FIGURE 3B

Rat and Human 5'UTR/promoter sequence

```
RAT
FEATURES          Location/Qualifiers
    misc_feature  294..410  ="homologous between rat and human"
    misc_feature  499..501  ="atg"
    misc_feature  371..498  ="5' utr"

BASE COUNT        78 a    176 c    173 g     74 t
ORIGIN
        1 gccaccaagc ggcgctcagc taccgtctag aaaggacttc tctaactttc ccacagggtt
       61 ccaagttttg ctttgcaagt gtcagaaaag gtcaatctac aagtttaggg aatactccca
      121 agggcccgaa cagtgccgca gcctcaggcg ggctgcggca gagccgagtc ccgggacgta
      181 gggctcctcg ggtggcagcg gcggggtacg ggcccgcccg ttccgggacc ggcttggcga
      241 gggctcggag ctgcgaggag ctgaggagca cccgggcccc ccgccctccc cagccggccg
      301 ctcctcccct gggtgggtcc ccgcgccctt tctggcgggg tctatttgca tagaaggaac
      361 tgcccgcagt ggccgctgcg tctgagcggg cggctagggg ggcgtgcgcg atccacggcc
      421 gcccggacgc cgagccccgc agccgccgac ctggagccac cccgggccgc agcgcctacg
      481 cagagccggc cggtcgccAT G
```

```
HUMAN
FEATURES          Location/Qualifiers
    misc_feature  347..466  ="homologous between rat and human"
    misc_feature  248..608  ="cDNA"
    misc_feature  606..608  ="predicted translation start codon"

BASE COUNT        83 a    201 c    217 g    107 t
ORIGIN
        1 gacccactca gttttttgca ggatttgaag ttttgaactt ttacaagtgt cagaaaggta
       61 attcacaagt ttagaggaat gtgctaaggc acgagtggtg ggtgctccag ccaggggtgg
      121 gctgcagaag gggcgcggtg tcgccgggct cccctccgac ctctggggtc cacagtgcgg
      181 gcttgggctg gggaagcctc agaggtgcgt gcggggcgg gtgccggcgc ccgggctagg
      241 tgagggcaga ggtgcgcgct gcgcgtggga tcagcccggc gccgacgggt ggctccgagg
      301 agctcgctcc ttcctcgccc ccgcccctc gccgcgcggg gccagccgg ccgctcctcc
      361 cctgggtggg tccctgctcc ttttctggca gggtctattt gcatagagga aactgcccaa
      421 agtggccgct gtggaggagc tggctgcggc gaaggggcg tgcgcggcgc tccgctgcta
      481 cccggaggct aaccccgcg cccggcggac ctcgtgcctc gggctgtccc gcctgctcct
      541 ctcgcaccca gcctctgccc cagcagcacc gcccctcgg agagtccacg cgcgacgaac
      601 gcgccATG
```

FIGURE 4

Correlation of CLG immunohistochemical staining with Gleason grade in human prostate tumors Expression of CLG in human tumor cell lines by RT-PCR analysis

| TUMOR | CELL LINE | CLG EXPRESSION |
|---|---|---|
| Prostate | LNCaP | - |
| | 22Rv1 | - |
| | PC-3 | - |
| | PC-3M | + |
| | PC-3pro4 | - |
| | PC-3LN4 | + |
| | DU145 | + |
| Breast | MDA-231 | - |
| | MDA-435 | + |
| Pancreas | BxPC-3 | - |
| | ASPC-1 | + |
| Ovary | OVCAR-1 | - |
| Colon | HT-29 | + |
| Leukemia | HL-60 | + |
| | K562 | + |
| Kidney | 786.0 | - |
| | Caki-1 | - |
| | Caki-2 | + |

FIGURE 6

Collagen
XXIII

Human  1 M G P G E R A G G G G D A G K G N A A G G G G G G R S A T T A G S R A V S A L C L L L S V G S A A A
Rat    1 M G A G E R A A G G G G T Q D - - - - - - - - - - - P G A G C G A R A L G A L C L L L S V G S A T A 51 C L L L G V Q A A A L Q G R V A A L E E E R E L L R R A G P P G A L D A W A E P H L E R L L R E K L
 40 C L L L G A Q A A A L H G R V A A L E Q E R E L L R R A G P S G A L A A W A E T H L E R L L R E K L
                              ▼ Cleavage site
101 D G L A K I R T A R E A P S E C V C P P G P P G R R G K P G R R G D P G P P G Q S G R D G Y P G P L
 90 D G V A K L R T V R E A P S E C I C P P G P P G R R G K P G R R G D P G P P G Q S G R D G Y P G P L 151 G L D G K P G L P G P K G E K G A P G D F G P R G D Q G Q D G A A G P P G P P G P P G A R G P P G D
140 G L D G K P G L P G P K G E K G A P G D F G P R G A Q G Q D G A A G P P G P P G P P G A R G P P G D 201 T G K D P G R G A Q G P A G P K G E P G Q D G E M G P K G P P G P K G E P G V P G K K G D D G T P S
190 T G K D G P R G A Q G P E G P R G E S G Q D G E M G P M G P P G P K G E P G T P G K K G D D G I P S 251 Q P G P P G P K G A S L S A L S P S Q E L G V I L M P C S P N P S Q R H Q I L A R Q S P K C P L S P
240 Q P G L P G P P G - - - - - - - - - - - - - - - - - - - - - - - - - - - - - - - - - - - - - - -

```
LOCUS       AY158895                3067 bp    mRNA    linear   PRI 07-JAN-2003
DEFINITION  Homo sapiens alpha 1 type XXIII collagen (COL23A1) mRNA, complete
            cds.
ACCESSION   AY158895
VERSION     AY158895
KEYWORDS    .
SOURCE      Homo sapiens (human)
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 3067)
  AUTHORS   Banyard,J., Bao,L. and Zetter,B.R.
  TITLE     Type XXIII collagen: a new transmembrane collagen upregulated in
            metastatic tumor cells
  JOURNAL   Unpublished
REFERENCE   2  (bases 1 to 3067)
  AUTHORS   Banyard,J., Bao,L. and Zetter,B.R.
  TITLE     Direct Submission
  JOURNAL   Submitted (04-OCT-2002) Department of Surgery, Children's Hospital,
            300 Longwood Ave., Boston, MA 02115, USA
FEATURES             Location/Qualifiers
     source          1..3067
                     /organism="Homo sapiens"
                     /db_xref="taxon:9606"
                     /chromosome="5"
                     /map="5q35"
     gene            1..3067
                     /gene="COL23A1"
     CDS             359..1981
                     /gene="COL23A1"
                     /codon_start=1
                     /product="alpha 1 type XXIII collagen"
                     /protein_id="AAO18361"
                     /translation="MGPGERAGGGGDAGKGNAAGGGGGGRSATTAGSRAVSALCLLLS
                     VGSAAACLLLGVQAAALQGRVAALEEERELLRRAGPPGALDAWAEPHLERLLREKLDG
                     LAKIRTAREAPSECVCPPGPPGRRGKPGRRGDPGPPGQSGRDGYPGPLGLDGKPGLPG
                     PKGEKGAPGDFGPRGDQGQDGAAGPPGPPGPPGARGPPGDTGKDGPRGAQGPAGPKGE
                     PGQDGEMGPKGPPGPKGEPGVPGKKGDDGTPSQPGPPGPKGEPGSMGPRGENGVDGAP
                     GPKGEPGHRGTDGAAGPRGAPGLKGEQGDTVVIDYDGRILDALKGPPGPQGPPGPPGI
                     PGAKGELGLPGAPGIDGEKGPKGQKGDPGEPGPAGLKGEAGEMGLSGLPGADGLKGEK
                     GESASDSLQESLAQLIVEPGPPGPPGPPGPMGLQGIQGPKGLDGAKGEKGASGERGPS
                     GLPGPVGPPGLIGLPGTKGEKGRPGEPGLDGFPGPRGEKGDRSERGEKGERGVPGRKG
                     VKGQKGEPGPPGLDQPCPVGPDGLPVPGCWHK"
BASE COUNT      606 a    945 c   1074 g    442 t
ORIGIN
        1 agaggtgcgc gctgcgcgtg ggatcagccc ggcgccgacg ggtggctccg aggagctcgc
       61 tccttcctcg cccccgcccc ctcgcgcgcg ggggccagcc cggccgctcc tcccctgggt
      121 gggtccctgc tcctttctg gcagggtcta tttgcataga ggaaactgcc caaagtggcc
      181 gctgtggagg agctggctgc ggcgaagggg gcgtgcgcgg cgatccgctg ctacccggag
      241 gctaaccccc gcgcccggcg gacctcgtgc ctcgggctgt ccgcctgct cctctcgcac
      301 ccagcctctg ccccagcagc accgcccct cggagagtcc acgcgcgacg aacgcgccat
      361 gggcccaggc gagcgcgccg gtggcggcg cgacgcgggg aagggcaatg cggcgggcgg
      421 cggcggcgga gggcgctcgg cgacgacggc cgggtccgg gcggtgagcg cgctgtgcct
      481 gctgctctcc gtgggctcgg cggctgcctg cctgctgctg ggtgtccagg cggccgcgct
      541 gcagggccgg gtggcggcgc tcgaggagga gcgggagctg ctgcgccgcg cggggccgcc
      601 aggcgccctg gacgcctggg ccgagccgca cctggagcgc ctgctgcggg agaagttgga
      661 cggactagcg aagatccgga ctgctcggga agctccatcc gaatgtgtct gcccccagg
      721 gccccctgga cggcgcgca agcctgggag aagaggcgac cctggtcctc cagggcaatc
      781 aggacgagat ggctaccgg gaccctgg tttggatggc aagcccggac ttccaggccc
      841 gaaaggggaa aagggtgcac caggagactt tggccccgg ggagaccaag gacaagatgg
      901 agctgctggg cctccggggc ccctggacc tcctggggcc cggggccctc ctggcgacac
```

FIGURE 8A

```
 961 tgggaaagat ggccccaggg gagcacaagg cccagcgggc ccaaaggag agcccggaca
1021 agacggcgag atgggcccaa agggaccccc agggcccaag ggtgagcctg gagtacctgg
1081 aaagaagggc gacgatggga caccaagcca gcctggacca ccagggccca agggcgagcc
1141 agggagcatg gggcctcggg gagagaacgg tgtggacggt gccccaggac cgaaggggga
1201 gcctgccac cgaggcacgg atggagctgc agggccccgg ggtgcccag gcctcaaggg
1261 cgagcaggga gacacagtgg tgatcgacta tgatggcagg atcttggatg ccctcaaggg
1321 gcctcccgga ccacaggggc cccagggcc accagggatc cctggagcca agggcgagct
1381 tggattgccc ggtgccccag gaatcgatgg agagaagggc cccaaggac agaaaggaga
1441 cccaggagag cctggccag caggactcaa aggggaagca ggcgagatgg gcttgtccgg
1501 cctccgggc gctgacgcc tcaaggggga aaggggag tcggcgtctg acagcctaca
1561 ggagagcctg gctcagctca tagtggagcc agggcccct ggccccctg gcccccagg
1621 cccgatgggc ctccaggaa tccagggtcc caagggcttg gatggagcaa agggagagaa
1681 gggtgcgtcg ggtgagagag gcccagcgg cctgcctggg ccagttggcc caccgggcct
1741 tattgggctg ccaggaacca aggagagaa gggcagaccc ggggagccag gactagatgg
1801 tttccctgga cccgaggag agaaggtga tcggagcgag cgtggagaga agggagaacg
1861 aggggtcccc ggccggaaag gagtgaaggg ccagaaggc gagccgggac caccaggcct
1921 ggaccagccg tgtcccgtgg gcccgacgg gctgcctgtg cctggctgct ggcataagtg
1981 acccacaggc ccagctcaca cctgtacaga tcgtgtgga cattttaat ttttgtaaaa
2041 acaaaacagt aatatattga tctttttca tggaatgcgc tacctgtggc cttttaacat
2101 tcaagagtat gcccacccag ccccaaagcc accggcatgt gaagctgcg gaaagtggac
2161 aggccagacc agggagatgt gtacctgagg ggcacccttg ggctgggct tcccaggaa
2221 ggagatgaag gtagaagcac ctggctcggg caaggctaga aagatgctac gttgggcctt
2281 cagtcacctg atcagcagag agactctcag ctgtggtact gcctgtaag aacctgccc
2341 cgcaaaactc tggagtccct gggacacacc ctatccaaga agacccaggg gtggaacagc
2401 ggctgctgtt gctcctggcc tcatcagcct ccaaactcaa ccacaaccag ctgcctctgc
2461 agttggacaa gacttggccc ccggacaaga ctcgccagc acttgcggct gggcccgggg
2521 agcagtgagt ggaaatcccc cacgagggtc tagctctacc acattcagga ggcctcagga
2581 ggccagcctg ccatgagagc acatgtcctc tggccaggag tagtggctga gctctgtgat
2641 cgctgtgatg tggacccagc tccagggagc agagtgtcgg ggatggaggg gcccagcctg
2701 gactgactgt acttcctgtc tctgtttcca ttatcaccca gagagggaca agataggaca
2761 tggcctggac caggagggca ggcctcccac tcagagtctg ggtctcactg gcccaagtc
2821 tccacccag aactctggcc aaaaatggct ctctaggtgg gctgtgcagg caaagcaaag
2881 ctcagggctg gttccagct ggcctgagca ggggcctgc caccagaccc acccacgctc
2941 tgacgagagg cttttccacc tcagcaagt gttcccagca accagctcca tcctggctgc
3001 ttgccttcca tttccgtgta gatggagatc actgtgtgta ataaccaca agtgcgtgtc
3061 aaaaaaa
```

FIGURE 8B

SEQUENCE LISTING

```
<160> NUMBER OF SEQ ID NOS: 14

<210> SEQ ID NO 1
<211> LENGTH: 3202
<212> TYPE: DNA
<213> ORGANISM: Homo sapiens

<400> SEQUENCE: 1
agaggtgcgc gctgcgcgtg ggatcagccc ggcgccgacg ggtggctccg aggagctcgc      60
tccttcctcg cccccgcccc ctcgccgcgc ggggccagcc cggccgctcc tcccctgggt     120
gggtccctgc tccttttctg gcagggtcta tttgcataga ggaaactgcc caaagtggcc     180
gctgtggagg agctggctgc ggcgaagggg gcgtgcgcgg cgatccgctg ctacccggag     240
gctaaccccc gcgcccggcg gacctcgtgc ctcgggctgt cccgcctgct cctctcgcac     300
ccagcctctg ccccagcagc accgcccct cggagagtcc acgcgcgacg aacgcgccat     360
gggcccaggc gagcgcgccg gtggcggcgg cgacgcgggg aagggcaatg cggcgggcgg     420
cggcggcgga gggcgctcgg cgacgacggc cgggtcccgg gcggtgagcg cgctgtgcct     480
gctgctctcc gtgggctcgg cggctgcctg cctgctgctg ggtgtccagg cggccgcgct     540
gcagggccgg gtggcggcgc tcgaggagga gcgggagctg ctgcggcgcg cggggccgcc     600
```

```
aggcgccctg gacgcctggg ccgagccgca cctggagcgc tgctgcggg agaagttgga      660 cggactagcg aagatccgga ctgctcggga agctccatcc gaatgtgtct gcccccagg     720 gcccctgga cggcgcggca agcctggag aagaggcgac cctggtcctc cagggcaatc      780
aggacgagat ggctacccgg gaccctggg tttggatggc aagcccggac ttccaggccc      840
gaaaggggaa aagggtgcac caggagactt tggcccccgg ggagaccaag acaagatgg     900 agctgctggg cctccggggc ccctggacc tcctggggcc cggggccctc ccgacactgg     960
gaaagatggc cccaggggag cacaaggccc agcgggcccc aaaggagagc ccggacaaga    1020
cggcgagatg ggcccaaagg accccccagg gcccaagggt gagcctggag tacctggaaa    1080
gaagggcgac gatgggacac caagccagcc tggaccacca gggcccaagg gggcctcact    1140
ctctgccctg tccccaagcc aggaactggg tgtcatcctc atgccttgct cccccaaccc    1200
ctcgcaacgc caccaaatcc tggccaggca gtctccaaaa tgtcccttga gccctggct    1260 gccccaaggc gagccaggga gcatgggcc tcggggagag aacggtgtgg acggtgcccc    1320
aggaccgaag ggggagcctg gccaccgagg cacggatgga gctgcagggc ccggggtgc     1380 cccaggcctc aagggcgagc agggagacac agtggtgatc gactatgatg caggatcttt    1440
ggatgccctc aaggggcctc ccggaccaca ggggccccca gggccaccag ggatccctgg    1500
agccaagggc gagcttggat tgcccggtgc cccaggaatc gatggagaga agggccccaa    1560
aggacagaaa ggagacccag gagagcctgg gccagcagga ctcaaagggg aagcaggcga    1620
gatgggcttg tccggcctcc cgggcgctga cggcctcaag ggggagaagg gggagtcggc    1680
gtctgacagc ctacaggaga gcctggctca gctcatagtg gagccagggc cccctggccc    1740
ccctggcccc ccaggcccga tgggcctcca gggaatccag ggtcccaagg gcttggatgg    1800
agcaaaggga gagaagggtg cgtcgggtga gagaggcccc agcggcctgc ctgggccagt    1860
tggcccaccg ggccttattg ggctgccagg aaccaaagga gagaagggca gacccgggga    1920
gccaggacta gatggtttcc ctggaccccg aggagagaaa ggtgatcgga gcgagcgtgg    1980
agagaaggga gaacgagggg tccccggccg gaaaggagtg aagggccaga agggcgagcc    2040
gggaccacca ggcctggacc agccgtgtcc cgtgggcccc gacgggctgc ctgtgcctgg    2100
ctgctggcat aagtgaccca caggcccagc tcacacctgt acagatccgt gtggacattt    2160
ttaatttttg taaaaacaaa acagtaatat attgatcttt tttcatggaa tgcgctacct    2220
gtggcctttt aacattcaag agtatgccca cccagcccca aagccaccgg catgtgaagc    2280
tgccggaaag tggacaggcc agaccaggga gatgtgtacc tgaggggcac ccttgggcct    2340
gggctttccc aggaaggaga tgaaggtaga agcacctggc tcgggcaagg ctagaaagat    2400
gctacgttgg gccttcagtc acctgatcag cagagagact ctcagctgtg gtactgcct     2460 gtaagaacct gccccgcaa aactctggag tccctgggac acacctatc caagaagacc      2520 cagggggtgga acagcggctg ctgttgctcc tggcctcatc agcctccaaa ctcaaccaca    2580
accagctgcc tctgcagttg acaagacttt ggcccccgga caagactcgc ccagcacttg    2640
cggctgggcc cggggagcag tgagtggaaa tccccccacga gggtctagct ctaccacatt    2700
caggaggcct caggaggcca gcctgccatg agagcacatg tcctctggcc aggagtagtg    2760
gctgagctct gtgatcgctg tgatgtggac ccagctccag ggagcagagt gtcggggatg    2820
gaggggccca gcctggactg actgtacttc ctgtctctgt ttccattatc acccagagag    2880
ggacaagata ggacatggcc tggaccaggg aggcaggcct cccactcaga gtctgggtct    2940
cactggcccc aagtctccca cccagaactc tggccaaaaa tggctctcta ggtgggctgt    3000
```

-continued

```
gcaggcaaag caaagctcag ggctggttcc cagctggcct gagcaggggg cctgccacca    3060
gacccaccca cgctctgacg agaggctttt ccacctccag caagtgttcc cagcaaccag    3120
ctccatcctg gctgcttgcc ttccatttcc gtgtagatgg agatcactgt gtgtaataaa    3180
ccacaagtgc gtgtcaaaaa aa                                             3202
```

<210> SEQ ID NO 2
<211> LENGTH: 585
<212> TYPE: PRT
<213> ORGANISM: Homo sapiens

<400> SEQUENCE: 2

```
Met Gly Pro Gly Glu Arg Ala Gly Gly Gly Asp Ala Gly Lys Gly
 1               5                  10                  15

Asn Ala Gly Gly Gly Gly Gly Arg Ser Ala Thr Thr Ala Gly
                20                  25                  30

Ser Arg Ala Val Ser Ala Leu Cys Leu Leu Ser Val Gly Ser Ala
             35                  40                  45

Ala Ala Cys Leu Leu Leu Gly Val Gln Ala Ala Leu Gln Gly Arg
 50                  55                  60

Val Ala Ala Leu Glu Glu Arg Glu Leu Leu Arg Arg Ala Gly Pro
 65                  70                  75                  80

Pro Gly Ala Leu Asp Ala Trp Ala Glu Pro His Leu Glu Arg Leu Leu
                85                  90                  95

Arg Glu Lys Leu Asp Gly Leu Ala Lys Ile Arg Thr Ala Arg Glu Ala
             100                 105                 110

Pro Ser Glu Cys Val Cys Pro Pro Gly Pro Pro Gly Arg Arg Gly Lys
         115                 120                 125

Pro Gly Arg Arg Gly Asp Pro Gly Pro Gly Gln Ser Gly Arg Asp
 130                 135                 140

Gly Tyr Pro Gly Pro Leu Gly Leu Asp Gly Lys Pro Gly Leu Pro Gly
145                 150                 155                 160

Pro Lys Gly Glu Lys Gly Ala Pro Gly Asp Phe Gly Pro Arg Gly Asp
                 165                 170                 175

Gln Gly Gln Asp Gly Ala Ala Gly Pro Pro Gly Pro Pro Gly Pro Pro
             180                 185                 190

Gly Ala Arg Gly Pro Pro Asp Thr Gly Lys Asp Gly Pro Arg Gly Ala
         195                 200                 205

Gln Gly Pro Ala Gly Pro Lys Gly Glu Pro Gly Gln Asp Gly Glu Met
     210                 215                 220

Gly Pro Lys Gly Pro Pro Gly Pro Lys Gly Glu Pro Gly Val Pro Gly
225                 230                 235                 240

Lys Lys Gly Asp Asp Gly Thr Pro Ser Gln Pro Gly Pro Pro Gly Pro
                 245                 250                 255

Lys Gly Ala Ser Leu Ser Ala Leu Ser Pro Ser Gln Glu Leu Gly Val
             260                 265                 270

Ile Leu Met Pro Cys Ser Pro Asn Pro Ser Gln Arg His Gln Ile Leu
         275                 280                 285

Ala Arg Gln Ser Pro Lys Cys Pro Leu Ser Pro Trp Leu Pro Gln Gly
     290                 295                 300

Glu Pro Gly Ser Met Gly Pro Arg Gly Glu Asn Gly Val Asp Gly Ala
305                 310                 315                 320

Pro Gly Pro Lys Gly Glu Pro Gly His Arg Gly Thr Asp Gly Ala Ala
                 325                 330                 335

Gly Pro Arg Gly Ala Pro Gly Leu Lys Gly Glu Gln Gly Asp Thr Val
```

```
                  340                 345                 350
Val Ile Asp Tyr Asp Gly Arg Ile Leu Asp Ala Leu Lys Gly Pro Pro
            355                 360                 365

Gly Pro Gln Gly Pro Pro Gly Pro Gly Ile Pro Gly Ala Lys Gly
        370                 375                 380

Glu Leu Gly Leu Pro Gly Ala Pro Gly Ile Asp Gly Glu Lys Gly Pro
385                 390                 395                 400

Lys Gly Gln Lys Gly Asp Pro Gly Glu Pro Gly Ala Gly Leu Lys
                405                 410                 415

Gly Glu Ala Gly Glu Met Gly Leu Ser Gly Leu Pro Gly Ala Asp Gly
            420                 425                 430

Leu Lys Gly Glu Lys Gly Glu Ser Ala Ser Asp Ser Leu Gln Glu Ser
        435                 440                 445

Leu Ala Gln Leu Ile Val Glu Pro Gly Pro Pro Gly Pro Pro Gly Pro
    450                 455                 460

Pro Gly Pro Met Gly Leu Gln Gly Ile Gln Gly Pro Lys Gly Leu Asp
465                 470                 475                 480

Gly Ala Lys Gly Glu Lys Gly Ala Ser Gly Glu Arg Gly Pro Ser Gly
                485                 490                 495

Leu Pro Gly Pro Val Gly Pro Pro Gly Leu Ile Gly Leu Pro Gly Thr
            500                 505                 510

Lys Gly Glu Lys Gly Arg Pro Gly Glu Pro Gly Leu Asp Gly Phe Pro
        515                 520                 525

Gly Pro Arg Gly Glu Lys Gly Asp Arg Ser Glu Arg Gly Glu Lys Gly
    530                 535                 540

Glu Arg Gly Val Pro Gly Arg Lys Gly Val Lys Gly Gln Lys Gly Glu
545                 550                 555                 560

Pro Gly Pro Pro Gly Leu Asp Gln Pro Cys Pro Val Gly Pro Asp Gly
                565                 570                 575

Leu Pro Val Pro Gly Cys Trp His Lys
            580                 585

<210> SEQ ID NO 3
<211> LENGTH: 2733
<212> TYPE: DNA
<213> ORGANISM: Rattus norvegicus

<400> SEQUENCE: 3
ggccgctgcg tctgagcggg cggctagggg ggcgtgcgcg atccacggcc gcccggacgc      60
cgagccccgc agccgccgac ctggagccac cccgggccgc agcgcctacg cagagccggc    120
cggtcgccat gggcgcgggc gagcgcgcgg cgggcggggg aggcacgcag acccccggcg    180
cgggctgcgg ggcgcgggcg ctgggcgcgc tgtgcctgct gctgtcggtg ggctctgcga    240
ccgcctgtct cctgctgggc gcccaagcgg ccgccttgca tggccgagtg gcggcgctgg    300
agcaggagcg cgaactgttg cggcgtgcgg ggccgtccgg agccctggcg gctgggccg     360 aaacgcacct ggagcgcctg ctacgggaga agttggatgg agtcgccaag ctcaggacag    420
ttcgagaagc ccctctgag tgcatctgtc ccctggtcc cctggacgg cgtggcaagc       480 cgggacgaag aggcgaccca ggccctccgg ggcaatcagg acgagatggc tacccgggac    540
ctctaggtct ggacggcaag ccaggactc caggccccaa aggggaaaag ggtgcaccag     600
gagactttgg cccacgggga gcccaagggc aagatggagc tgcaggacca cctgggcctc    660
ctgggccacc tggggcccgg ggccctcctg gtgacactgg gaaagatggt ccccgaggag    720
ctcaaggccc agagggtccc agaggagagt ctggacaaga tggcgaaatg ggcccccatgg   780
```

-continued

```
gacctccagg acccaaggga gaacctggca ctcctggaaa gaaggggat gatgggatac    840
ccagccagcc aggactccct ggaccccag ggcccaaggg tgagccagga gatgtgggc     900
cccaaggaga gactggagta gacggtgccc ctggactgaa gggggagccc ggtcacccag   960
gcacggatgg agccataggg ccccggggtc ccccgggcct caagggagaa caaggtgaca  1020
cggtggtaat cgactatgat ggcaggatct tagatgccct gaagggtcct cccggaccac  1080
agggagctcc tgggccacca gggatccctg gagccaaggg tgaacttgga ttgcctggtg  1140
ctccaggaat cgatggagag aagggtccca aggaccaaa aggagaccca ggagagcctg   1200
gaccagctgg acccaagggg gaaacaggag agatgggcct gtcaggtctt ccgggtgccg  1260
atggtcccaa gggagaaaag ggagagtcag catctgacca tctacaggag agcctggccc  1320
agatcatagt ggagccaggg ccccccggtc tcctgggcc ccccggcccc atgggccttc   1380
aggggatcca gggtcccaag ggcctggatg gagccaaggg agaaaagggt gcatcgggtg  1440
agagaggccc tcacggtctg cctggaccag ttggcccacc aggccttatt gggttgcccg  1500
gaaccaaagg agagaagggc cgaccccgga gccaggact cgacggtttc cctggaccca   1560
ggggagagaa aggcgaccga agtgaacgag agagaaggg ggagcgagga gttcctggtc   1620
ggaaaggagt gaaaggccag aagggagagc caggcccacc aggccttgac cagccatgcc  1680
ctgtgggccc cgacggttg cctgtgcctg gttgctggca taagtgatcc tcgggcatag   1740
cccccaacct gtacagatcc gtttggatgt ttttaactcg tgtaaaaaca aacagtaat   1800
atattgaact tctttatggg atgcgccaac tgtgtggcct tgtaagattt gcaagtgtgc  1860
caaccagccc ctggaccatc tgcacaggaa gccggcagga acgcagacag gctggctgct  1920
ctggggaaac ttgtgttcga aggccccgg cagggcctgg ctttcccagg gagaggacga   1980
gggtgaaaac gcctggctca ggtgaggatg gacagactcc aggtcgggct acaatcacc   2040
tgattagcag agacttacaa caactgtcct ctgaaacccc actgcccaa cttctcactg   2100
tccaacgaca ccccttgga cacctgctgt accctcttgc ttctggactg tgccacaggc   2160
agctgcactg ggaccctagg tttaacaggg caggcgaaga ttcctagagt ccagcacttg  2220
gggagaaggc aatggaagaa cccaagaggg ccttgctcca cccagttcag taggcttcct  2280
gacacaggag cttgtaccct cttcagacct tgggaaatgg caagactctg tggataccc   2340
actggcaggc agcccagtga accctgactg tagggtgaag aggccatacc cactagttgg  2400
tacttcctgt ctcctcaccc agagcaggaa caggaagtgg cttgtcagc caaggagac    2460
aggcctcctg ttcagaactt gtatctcact ggccccaagt ctctgaccta gacctctggt  2520
tagcctgaca gaaacaggcc cctagtaaa tgacccctgaa ggctggtccc ccggcaagcc  2580
tgagcaaagc acctgtgact gaaacccctg ccctctctgg agaggcttga acacctataa  2640
cgaagtttcc tagctcctgc tccatcacgg cctcacatcc ctctgcatat aaaggcacca  2700
tgagcaataa accacaaatg tgcgtccagt aaa                                2733
```

<210> SEQ ID NO 4
<211> LENGTH: 532
<212> TYPE: PRT
<213> ORGANISM: Rattus norvegicus

<400> SEQUENCE: 4

```
Met Gly Ala Gly Glu Arg Ala Ala Gly Gly Gly Thr Gln Asp Pro
 1               5                  10                  15

Gly Ala Gly Cys Gly Ala Arg Ala Leu Gly Ala Leu Cys Leu Leu Leu
                20                  25                  30
```

```
Ser Val Gly Ser Ala Thr Ala Cys Leu Leu Gly Ala Gln Ala Ala
         35                  40                  45
Ala Leu His Gly Arg Val Ala Leu Glu Gln Arg Glu Leu Leu
 50                  55                  60
Arg Arg Ala Gly Pro Ser Gly Ala Leu Ala Ala Trp Ala Glu Thr His
 65                  70                  75                  80
Leu Glu Arg Leu Leu Arg Glu Lys Leu Asp Gly Val Ala Lys Leu Arg
                 85                  90                  95
Thr Val Arg Glu Ala Pro Ser Glu Cys Ile Cys Pro Gly Pro Pro
             100                 105                 110
Gly Arg Gly Lys Pro Gly Arg Gly Asp Pro Gly Pro Gly
         115                 120                 125
Gln Ser Gly Arg Asp Gly Tyr Pro Gly Pro Leu Gly Leu Asp Gly Lys
         130                 135                 140
Pro Gly Leu Pro Gly Pro Lys Gly Glu Lys Gly Ala Pro Gly Asp Phe
145                 150                 155                 160
Gly Pro Arg Gly Ala Gln Gly Gln Asp Gly Ala Ala Gly Pro Pro Gly
                165                 170                 175
Pro Pro Gly Pro Pro Gly Ala Arg Gly Pro Pro Gly Asp Thr Gly Lys
            180                 185                 190
Asp Gly Pro Arg Gly Ala Gln Gly Pro Glu Gly Pro Arg Gly Glu Ser
            195                 200                 205
Gly Gln Asp Gly Glu Met Gly Pro Met Gly Pro Pro Gly Pro Lys Gly
        210                 215                 220
Glu Pro Gly Thr Pro Gly Lys Lys Gly Asp Asp Gly Ile Pro Ser Gln
225                 230                 235                 240
Pro Gly Leu Pro Gly Pro Pro Gly Pro Lys Gly Glu Pro Gly Asp Val
                245                 250                 255
Gly Pro Gln Gly Glu Thr Gly Val Asp Gly Ala Pro Gly Leu Lys Gly
            260                 265                 270
Glu Pro Gly His Pro Gly Thr Asp Gly Ala Ile Gly Pro Arg Gly Pro
            275                 280                 285
Pro Gly Leu Lys Gly Glu Gln Gly Asp Thr Val Val Ile Asp Tyr Asp
        290                 295                 300
Gly Arg Ile Leu Asp Ala Leu Lys Gly Pro Pro Gly Pro Gln Gly Ala
305                 310                 315                 320
Pro Gly Pro Pro Gly Ile Pro Gly Ala Lys Gly Glu Leu Gly Leu Pro
                325                 330                 335
Gly Ala Pro Gly Ile Asp Gly Glu Lys Gly Pro Lys Gly Pro Lys Gly
            340                 345                 350
Asp Pro Gly Glu Pro Gly Pro Ala Gly Pro Lys Gly Glu Thr Gly Glu
            355                 360                 365
Met Gly Leu Ser Gly Leu Pro Gly Ala Asp Gly Pro Lys Gly Glu Lys
        370                 375                 380
Gly Glu Ser Ala Ser Asp His Leu Gln Glu Ser Leu Ala Gln Ile Ile
385                 390                 395                 400
Val Glu Pro Gly Pro Pro Gly Pro Pro Gly Pro Pro Gly Pro Met Gly
                405                 410                 415
Leu Gln Gly Ile Gln Gly Pro Lys Gly Leu Asp Gly Ala Lys Gly Glu
            420                 425                 430
Lys Gly Ala Ser Gly Glu Arg Gly Pro His Gly Leu Pro Gly Pro Val
        435                 440                 445
Gly Pro Pro Gly Leu Ile Gly Leu Pro Gly Thr Lys Gly Glu Lys Gly
```

```
                450                 455                 460
Arg Pro Gly Glu Pro Gly Leu Asp Gly Phe Pro Gly Pro Arg Gly Glu
465                 470                 475                 480

Lys Gly Asp Arg Ser Glu Arg Gly Glu Lys Gly Glu Arg Gly Val Pro
                485                 490                 495

Gly Arg Lys Gly Val Lys Gly Gln Lys Gly Glu Pro Gly Pro Pro Gly
            500                 505                 510

Leu Asp Gln Pro Cys Pro Val Gly Pro Asp Gly Leu Pro Val Pro Gly
        515                 520                 525

Cys Trp His Lys
    530

<210> SEQ ID NO 5
<211> LENGTH: 2024
<212> TYPE: DNA
<213> ORGANISM: Mus sp.

<400> SEQUENCE: 5
cggccgccct gcatggccga gtggcggcgc tggagcagga gcgcgagctg ttgcggcatg     60
cggggccgtc cggagccctg ccgcctgggc cgaaacgca cctggagcgc ctgttacggg     120
agaagttgga tggagtcgcc aagctcagga cagttcgaga gccccatct gagtgcatct     180 gtcccctgg tcccctgga cggcgtggca agcctgacg aagaggcgac cctggtcctc      240
cagggcaatc aggacgagat ggctacccgg gacctctagg tctggacggc aagcccggac     300
ttccaggccc caaggggaa aagggtgcac caggagactt ggcccacgg ggagcccaag      360 ggcaagatgg agctgcagga ccacctgggc ctcctgggcc acctggggcc cggggccctc     420
ctggtgacac tgggaaagat ggtccccgag gagctcaagg cccagaggt cccagaggag     480 agtctggaca agatggcgaa atgggcccca tgggacctcc aggacccaag ggagaacctg     540
gcactcctgg aaagaagggg gatgatggga tacccagcca gccaggactc cctggacccc     600
cagggcccaa gggtgagcca ggagatgtgg ggccccaagg agagactgga gtagacggtg     660
cccctggact gaaggggag cccggtcacc caggcacgga tggagccata gggcccggg      720 gtcccccggg cctcaaggga gaacaaggtg acacggtggt aatcgactat gatggcagga     780
tcttagatgc cctgaagggt cctccccggac cacagggagc tcctgggcca ccagggatcc     840
ctggagccaa gggtgaactt ggattgcctg gtgctccagg aatcgatgga gagaagggtc     900
ccaaaggacc aaaaggagac ccaggagagc ctggaccagc tgggcccaaa ggggaaacag     960
gagagatggg cctgtcaggt cttccgggtg ccgatggtcc caaggagaa aagggagagt     1020 cagcttctga ccatctacag gagagcctgg cccagatcat agtggagcca ggccccccg     1080 gtcctcctgg gcccccggc cccatgggcc ttcagggat ccagggtccc aagggcctgg      1140
atggagccaa gggagaaaag ggtacatcgg gtgagagagg ccctcacggc ctgcctggac     1200
cagttggccc accaggcctt attgggttgc aggaaccaa aggagagaag gcagacctg      1260 gagaaccagg actcgatggg ttccctggac caggggaga aaggggtgac cgaagtgaac     1320
gtggagagaa gggggagcga ggagttcctg gccggaaagg cgtgaagggc cagaagggag     1380
agccgggccc accaggcctt gaccagccat gtcctgtggg cccgatggg ttgcctgtgc      1440 ctggttgctg gcataagtga tcctcagaca taacccctga cctgtacaga tccgtttgga     1500
tgttttgaac tcatgtaaaa acaaaacagt aatatattga acttctttat gggatgcgcc     1560
aactgtggcc atgtaacatt tgcaagtgtg ccaaccagcc cctggacaat ctgcacagga     1620
agccagcagg aatgcggaca ggctgctctg aggaaacttc tgttcaaagg ccctgggtag     1680
```

```
ggcctggctt tcccagggaa gatgacgagg gtgaaaacgc ctggctcagg tgaggctgga    1740
cagactccag gttgggctca taatcacctg attagcagag acttgcaaca aactgtttcc    1800
tgaaacccca ttgcccagtt ctcactgtcc aatagcaccc ccttggacaa cttgcttgta    1860
gccttcttgc ttcgcggact gtgccgtag gcagttgcac tgggggccct atgtttccac     1920
aggggcccag caaagattct taaagtccag cacttggggg agaagggcct ggggagaacc    1980
ccgagaggcc ttggtccccc aatttaagcc cttccaaacc accg                     2024

<210> SEQ ID NO 6
<211> LENGTH: 485
<212> TYPE: PRT
<213> ORGANISM: Mus sp.

<400> SEQUENCE: 6

Ala Ala Leu His Gly Arg Val Ala Ala Leu Glu Gln Glu Arg Glu Leu
 1               5                  10                  15

Leu Arg His Ala Gly Pro Ser Gly Ala Leu Ala Ala Trp Ala Glu Thr
             20                  25                  30

His Leu Glu Arg Leu Leu Arg Glu Lys Leu Asp Gly Val Ala Lys Leu
         35                  40                  45

Arg Thr Val Arg Glu Ala Pro Ser Glu Cys Ile Cys Pro Pro Gly Pro
     50                  55                  60

Pro Gly Arg Arg Gly Lys Pro Gly Arg Arg Gly Asp Pro Gly Pro Pro
 65                  70                  75                  80

Gly Gln Ser Gly Arg Asp Gly Tyr Pro Gly Pro Leu Gly Leu Asp Gly
                 85                  90                  95

Lys Pro Gly Leu Pro Gly Pro Lys Gly Glu Lys Gly Ala Pro Gly Asp
            100                 105                 110

Phe Gly Pro Arg Gly Ala Gln Gly Gln Asp Gly Ala Ala Gly Pro Pro
        115                 120                 125

Gly Pro Pro Gly Pro Pro Gly Ala Arg Gly Pro Pro Gly Asp Thr Gly
    130                 135                 140

Lys Asp Gly Pro Arg Gly Ala Gln Gly Pro Glu Gly Pro Arg Gly Glu
145                 150                 155                 160

Ser Gly Gln Asp Gly Glu Met Gly Pro Met Gly Pro Pro Gly Pro Lys
                165                 170                 175

Gly Glu Pro Gly Thr Pro Gly Lys Lys Gly Asp Asp Gly Ile Pro Ser
            180                 185                 190

Gln Pro Gly Leu Pro Gly Pro Pro Gly Pro Lys Gly Glu Pro Gly Asp
        195                 200                 205

Val Gly Pro Gln Gly Glu Thr Gly Val Asp Gly Ala Pro Gly Leu Lys
    210                 215                 220

Gly Glu Pro Gly His Pro Gly Thr Asp Gly Ala Ile Gly Pro Arg Gly
225                 230                 235                 240

Pro Pro Gly Leu Lys Gly Glu Gln Gly Asp Thr Val Val Ile Asp Tyr
                245                 250                 255

Asp Gly Arg Ile Leu Asp Ala Leu Lys Gly Pro Pro Gly Pro Gln Gly
            260                 265                 270

Ala Pro Gly Pro Pro Gly Ile Pro Gly Ala Lys Gly Glu Leu Gly Leu
        275                 280                 285

Pro Gly Ala Pro Gly Ile Asp Gly Glu Lys Gly Pro Lys Gly Pro Lys
    290                 295                 300

Gly Asp Pro Gly Glu Pro Gly Pro Ala Gly Pro Lys Gly Glu Thr Gly
305                 310                 315                 320
```

```
Glu Met Gly Leu Ser Gly Leu Pro Gly Ala Asp Gly Pro Lys Gly Glu
            325                 330                 335

Lys Gly Glu Ser Ala Ser Asp His Leu Gln Glu Ser Leu Ala Gln Ile
            340                 345                 350

Ile Val Glu Pro Gly Pro Pro Gly Pro Gly Pro Pro Gly Pro Met
            355                 360                 365

Gly Leu Gln Gly Ile Gln Gly Pro Lys Gly Leu Asp Gly Ala Lys Gly
            370                 375                 380

Glu Lys Gly Thr Ser Gly Glu Arg Gly Pro His Gly Leu Pro Gly Pro
385                 390                 395                 400

Val Gly Pro Pro Gly Leu Ile Gly Leu Pro Gly Thr Lys Gly Glu Lys
                    405                 410                 415

Gly Arg Pro Gly Glu Pro Gly Leu Asp Gly Phe Pro Gly Pro Arg Gly
                    420                 425                 430

Glu Lys Gly Asp Arg Ser Glu Arg Gly Glu Lys Gly Glu Arg Gly Val
            435                 440                 445

Pro Gly Arg Lys Gly Val Lys Gly Gln Lys Gly Glu Pro Gly Pro Pro
450                 455                 460

Gly Leu Asp Gln Pro Cys Pro Val Gly Pro Asp Gly Leu Pro Val Pro
465                 470                 475                 480

Gly Cys Trp His Lys
            485

<210> SEQ ID NO 7
<211> LENGTH: 501
<212> TYPE: DNA
<213> ORGANISM: Rattus norvegicus

<400> SEQUENCE: 7
gccaccaagc ggcgctcagc taccgtctag aaaggacttc tctaactttc ccacagggtt      60
ccaagttttg ctttgcaagt gtcagaaaag gtcaatctac aagtttaggg aatactccca    120
agggcccgaa cagtgccgca gcctcaggcg ggctgcggca gagccgagtc ccgggacgta    180
gggctcctcg ggtggcagcg gcgggtacgg gcccgcccg ttccgggacc ggcttggcga    240
gggctcggag ctgcgaggag ctgaggagca ccgggcccc cgccctccc cagccggccg    300 ctcctcccct gggtgggtcc ccgcgccctt tctggcgggg tctatttgca tagaaggaac    360
tgcccgcagt ggccgctgcg tctgagcggg cggctagggg ggcgtgcgcg atccacggcc    420
gcccggacgc cgagcccgc agccgccgac ctggagccac ccgggccgc agcgcctacg    480 cagagccggc cggtcgccat g                                              501

<210> SEQ ID NO 8
<211> LENGTH: 608
<212> TYPE: DNA
<213> ORGANISM: Homo sapiens

<400> SEQUENCE: 8
gacccactca gttttttgca ggatttgaag ttttgaactt ttacaagtgt cagaaaggta     60
attcacaagt ttagaggaat gtgctaaggc acgagtggtg ggtgctccag ccaggggtgg    120
gctgcagaag gggcgcggtg tcgccgggct cccctccgac ctctgggtc acagtgcgg     180 gcttgggctg gggaagcctc agaggtgcgt gcggggggcgg gtgccggcgc ccgggctagg   240
tgagggcaga ggtgcgcgct gcgcgtggga tcagcccggc ccgacgggt ggctccgagg    300 agctcgctcc ttcctcgccc ccgccccctc gccgcgcggg gccagcccgg ccgctcctcc    360
```

```
cctgggtggg tccctgctcc ttttctggca gggtctattt gcatagagga aactgcccaa    420
agtggccgct gtggaggagc tggctgcggc aagggggcg tgcgcggcgc tccgctgcta    480
cccggaggct aaccccgcg cccggcggac ctcgtgcctc gggctgtccc gcctgctcct    540
ctcgcaccca gcctctgccc cagcagcacc gcccctcgg agagtccacg cgcgacgaac    600
gcgccatg                                                           608
```

<210> SEQ ID NO 9
<211> LENGTH: 16
<212> TYPE: PRT
<213> ORGANISM: Homo sapiens

<400> SEQUENCE: 9

Ala Ala Leu Glu Glu Glu Arg Glu Leu Leu Arg Arg Ala Gly Pro Pro
 1               5                  10                  15

<210> SEQ ID NO 10
<211> LENGTH: 16
<212> TYPE: PRT
<213> ORGANISM: Homo sapiens

<400> SEQUENCE: 10

Asp Thr Val Val Ile Asp Tyr Asp Gly Arg Ile Leu Asp Ala Leu Lys
 1               5                  10                  15

<210> SEQ ID NO 11
<211> LENGTH: 20
<212> TYPE: PRT
<213> ORGANISM: Homo sapiens

<400> SEQUENCE: 11

Lys Gly Glu Ser Ala Ser Asp Ser Leu Gln Glu Ser Leu Ala Gln Leu
 1               5                  10                  15

Ile Val Glu Pro
            20

<210> SEQ ID NO 12
<211> LENGTH: 3067
<212> TYPE: DNA
<213> ORGANISM: Homo sapiens

<400> SEQUENCE: 12

```
agaggtgcgc gctgcgcgtg ggatcagccc ggcgccgacg ggtggctccg aggagctcgc     60
tccttcctcg ccccgcccc ctcgccgcgc ggggccagcc cggccgctcc tcccctgggt    120
gggtccctgc tccttttctg gcagggtcta tttgcataga ggaaactgcc caaagtggcc    180
gctgtggagg agctggctgc ggcgaagggg cgtgcgcgg cgatccgctg ctaccccgag    240
gctaaccccc gcgcccggcg gacctcgtgc ctcgggctgt cccgcctgct cctctcgcac    300
ccagcctctg cccagcagc accgcccct cggagagtcc acgcgcgacg aacgcgccat    360
gggcccaggc gagcgcgccg gtggcggcgg cgacgcgggg aagggcaatg cggcgggcgg    420
cggcggcgga gggcgctcgg cgacgacggc cgggtcccgg gcgtgagcg cgctgtgcct    480 gctgctctcc gtgggctcgg cggctgcctg cctgctgctg ggtgtccagg cggccgcgct    540
gcagggccgg gtggcggcgc tcaggagga gcggagctg ctgcggcgcg cggggccgcc    600
aggcgccctg gacgcctggg ccgagccgca cctggagcgc ctgctgcggg agaagttgga    660
cggactagcg aagatccgga ctgctcggga agctccatcc gaatgtgtct gccccccagg    720 gcccctgga cggcgcggca agcctgggag aagaggcgac cctggtcctc cagggcaatc    780
```

```
aggacgagat ggctacccgg gaccccctggg tttggatggc aagcccggac ttccaggccc    840
gaaaggggaa aagggtgcac caggagactt tggcccccgg ggagaccaag gacaagatgg    900
agctgctggg cctccggggc cccctggacc tcctggggcc cggggccctc ctggcgacac    960
tgggaaagat ggccccaggg gagcacaagg cccagcgggc cccaaaggag agcccggaca   1020
agacggcgag atgggcccaa agggaccccc agggcccaag ggtgagcctg gagtacctgg   1080
aaagaagggc gacgatggga caccaagcca gcctggacca ccagggccca agggcgagcc   1140
agggagcatg gggcctcggg gagagaacgg tgtggacggt gccccaggac cgaaggggga   1200
gcctggccac cgaggcacgg atggagctgc agggcccccgg ggtgcccag gcctcaaggg   1260 cgagcaggga gacacagtgg tgatcgacta tgatggcagg atcttggatg ccctcaaggg   1320
gcctcccgga ccacagggc ccccagggcc accagggatc cctggagcca agggcgagct   1380
tggattgccc ggtgccccag gaatcgatgg agagaagggc cccaaaggac agaaaggaga   1440
cccaggagag cctgggccag caggactcaa agggaagca ggcgagatgg gcttgtccgg   1500
cctcccgggc gctgacggcc tcaaggggga aaggggggag tcggcgtctg acagcctaca   1560
ggagagcctg gctcagctca tagtggagcc agggccccct ggccccccctg gccccccagg   1620 cccgatgggc ctccagggaa tccagggtcc caagggcttg gatggagcaa agggagagaa   1680
gggtgcgtcg ggtgagagag gccccagcgg cctgcctggg ccagttggcc caccgggcct   1740
tattgggctg ccaggaacca aaggagagaa gggcagaccc ggggagccag gactagatgg   1800
tttccctgga ccccgaggag agaaaggtga tcggagcgag cgtggagaga agggagaacg   1860
aggggtcccc ggccggaaag gagtgaaggg ccagaagggc gagccgggac caccaggcct   1920
ggaccagccg tgtcccgtgg gccccgacgg gctgcctgtg cctggctgct ggcataagtg   1980
acccacaggc ccagctcaca cctgtacaga tccgtgtgga catttttaat ttttgtaaaa   2040
acaaaacagt aatatattga tcttttttca tggaatgcgc tacctgtggc cttttaacat   2100
tcaagagtat gcccacccag ccccaaagcc accggcatgt gaagctgccg gaaagtggac   2160
aggccagacc agggagatgt gtacctgagg ggcaccccttg ggcctgggct ttcccaggaa   2220
ggagatgaag gtagaagcac ctggctcggg caaggctaga aagatgctac gttgggcctt   2280
cagtcacctg atcagcagag agactctcag ctgtggtact gccctgtaag aacctgcccc   2340
cgcaaaactc tggagtccct gggacacacc ctatccaaga gacccaggg gtggaacagc   2400 ggctgctgtt gctcctggcc tcatcagcct ccaaactcaa ccacaaccag ctgcctctgc   2460
agttggacaa gacttggccc ccggacaaga ctcgcccagc acttgcggct gggcccgggg   2520
agcagtgagt ggaaatcccc cacgagggtc tagctctacc acattcagga ggcctcagga   2580
ggccagcctg ccatgagagc acatgtcctc tggccaggag tagtggctga gctctgtgat   2640
cgctgtgatg tggacccagc tcagggagc agagtgtcgg ggatggaggg gcccagcctg   2700
gactgactgt acttcctgtc tctgtttcca ttatcaccca gagagggaca agataggaca   2760
tggcctggac caggaggca ggcctcccac tcagagtctg ggtctcactg gccccaagtc   2820
tcccacccag aactctggcc aaaaatggct ctctaggtgg gctgtgcagg caaagcaaag   2880
ctcagggctg gttcccagct ggcctgagca ggggcctgc caccagaccc acccacgctc   2940
tgacgagagg cttttccacc tccagcaagt gttcccagca accagctcca tcctggctgc   3000
ttgccttcca tttccgtgta gatggagatc actgtgtgta ataaaccaca agtgcgtgtc   3060
aaaaaaa                                                             3067

<210> SEQ ID NO 13
```

```
<211> LENGTH: 540
<212> TYPE: PRT
<213> ORGANISM: Homo sapiens

<400> SEQUENCE: 13

Met Gly Pro Gly Glu Arg Ala Gly Gly Gly Asp Ala Gly Lys Gly
  1               5                  10                  15

Asn Ala Ala Gly Gly Gly Gly Gly Arg Ser Ala Thr Thr Ala Gly
             20                  25                  30

Ser Arg Ala Val Ser Ala Leu Cys Leu Leu Leu Ser Val Gly Ser Ala
         35                  40                  45

Ala Ala Cys Leu Leu Leu Gly Val Gln Ala Ala Leu Gln Gly Arg
     50                  55                  60

Val Ala Ala Leu Glu Glu Glu Arg Glu Leu Leu Arg Arg Ala Gly Pro
 65                  70                  75                  80

Pro Gly Ala Leu Asp Ala Trp Ala Glu Pro His Leu Glu Arg Leu Leu
                 85                  90                  95

Arg Glu Lys Leu Asp Gly Leu Ala Lys Ile Arg Thr Ala Arg Glu Ala
                100                 105                 110

Pro Ser Glu Cys Val Cys Pro Pro Gly Pro Pro Gly Arg Arg Gly Lys
                115                 120                 125

Pro Gly Arg Arg Gly Asp Pro Gly Pro Pro Gly Gln Ser Gly Arg Asp
            130                 135                 140

Gly Tyr Pro Gly Pro Leu Gly Leu Asp Gly Lys Pro Gly Leu Pro Gly
145                 150                 155                 160

Pro Lys Gly Glu Lys Gly Ala Pro Gly Asp Phe Gly Pro Arg Gly Asp
                165                 170                 175

Gln Gly Gln Asp Gly Ala Ala Gly Pro Pro Gly Pro Gly Pro Pro
                180                 185                 190

Gly Ala Arg Gly Pro Pro Gly Asp Thr Gly Lys Asp Gly Pro Arg Gly
            195                 200                 205

Ala Gln Gly Pro Ala Gly Pro Lys Gly Glu Pro Gly Gln Asp Gly Glu
        210                 215                 220

Met Gly Pro Lys Gly Pro Pro Gly Pro Lys Gly Glu Pro Gly Val Pro
225                 230                 235                 240

Gly Lys Lys Gly Asp Asp Gly Thr Pro Ser Gln Pro Gly Pro Pro Gly
                245                 250                 255

Pro Lys Gly Glu Pro Gly Ser Met Gly Pro Arg Gly Glu Asn Gly Val
            260                 265                 270

Asp Gly Ala Pro Gly Pro Lys Gly Glu Pro Gly His Arg Gly Thr Asp
        275                 280                 285

Gly Ala Ala Gly Pro Arg Gly Ala Pro Gly Leu Lys Gly Glu Gln Gly
    290                 295                 300

Asp Thr Val Val Ile Asp Tyr Asp Gly Arg Ile Leu Asp Ala Leu Lys
305                 310                 315                 320

Gly Pro Pro Gly Pro Gln Gly Pro Pro Gly Pro Pro Gly Ile Pro Gly
                325                 330                 335

Ala Lys Gly Glu Leu Gly Leu Pro Gly Ala Pro Gly Ile Asp Gly Glu
            340                 345                 350

Lys Gly Pro Lys Gly Gln Lys Gly Asp Pro Gly Glu Pro Gly Pro Ala
        355                 360                 365

Gly Leu Lys Gly Glu Ala Gly Glu Met Gly Leu Ser Gly Leu Pro Gly
    370                 375                 380

Ala Asp Gly Leu Lys Gly Glu Lys Gly Glu Ser Ala Ser Asp Ser Leu
385                 390                 395                 400
```

```
Gln Glu Ser Leu Ala Gln Leu Ile Val Glu Pro Gly Pro Gly Pro
                405                 410                 415

Pro Gly Pro Pro Gly Pro Met Gly Leu Gln Gly Ile Gln Gly Pro Lys
            420                 425                 430

Gly Leu Asp Gly Ala Lys Gly Glu Lys Gly Ala Ser Gly Glu Arg Gly
            435                 440                 445

Pro Ser Gly Leu Pro Gly Pro Val Gly Pro Pro Gly Leu Ile Gly Leu
    450                 455                 460

Pro Gly Thr Lys Gly Glu Lys Gly Arg Pro Gly Glu Pro Gly Leu Asp
465             470                 475                 480

Gly Phe Pro Gly Pro Arg Gly Glu Lys Gly Asp Arg Ser Glu Arg Gly
                485                 490                 495

Glu Lys Gly Glu Arg Gly Val Pro Gly Arg Lys Gly Val Lys Gly Gln
            500                 505                 510

Lys Gly Glu Pro Gly Pro Pro Gly Leu Asp Gln Pro Cys Pro Val Gly
            515                 520                 525

Pro Asp Gly Leu Pro Val Pro Gly Cys Trp His Lys
    530                 535                 540

<210> SEQ ID NO 14
<211> LENGTH: 20
<212> TYPE: PRT
<213> ORGANISM: Homo sapiens

<400> SEQUENCE: 14

Leu Asp Gln Pro Cys Pro Val Gly Pro Asp Gly Leu Pro Val Pro Gly
 1               5                  10                  15

Cys Trp His Lys
            20
```

METHODS FOR DIAGNOSIS AND PROGNOSIS OF CANCER

CROSS-REFERENCE TO RELATED APPLICATIONS

This application is the U.S. National Phase Entry Under 35 U.S.C. §371 of International Application No. PCT/US03/08100, filed Mar. 18, 2003 which designated the U.S and claimed priority under 35 U.S.C. §119(e) of U.S. Provisional Application No. 60/365,667 filed Mar. 19, 2002.

STATEMENT REGARDING FEDERALLY SPONSORED RESEARCH

The work described herein was supported, in part, by National Institute of Health grant No. 37393. The U.S. Government has certain rights to the invention.

FIELD OF THE INVENTION

The present invention relates to a novel DNA sequence and use of that sequence and its gene product in methods for the diagnosis and prognosis of cancer, particularly metastatic cancer.

BACKGROUND OF THE INVENTION

Cancer remains a major health concern. Despite increased understanding of many aspects of cancer, the methods available for its treatment continue to have limited success. First of all, the number of cancer therapies is limited, and none provides an absolute guarantee of success. Second, there are many types of malignancies, and the success of a particular therapy for treating one type of cancer does not mean that it will be broadly applicable to other types. Third, many cancer treatments are associated with toxic side effects. Most treatments rely on an approach that involves killing off rapidly growing cells; however, these treatments are not specific to cancer cells and can adversely affect any dividing healthy cells. Fourth, assessing molecular changes associated with cancerous cells remains difficult. Given these limitations in the current arsenal of anti-cancer treatments, how can the best therapy for a given patient be designed? The ability to detect a malignancy as early as possible, and assess its severity, is extremely helpful in designing an effective therapeutic approach. Thus, methods for detecting the presence of malignant cells and understanding their disease state are desirable, and will contribute to our ability to tailor cancer treatment to a patient's disease.

While different forms of cancer have different properties, one factor which many cancers share is the ability to metastasize. Until such time as metastasis occurs, a tumor, although it may be malignant, is confined to one area of the body. This may cause discomfort and/or pain, or even lead to more serious problems including death, but if it can be located, it may be surgically removed and, if done with adequate care, be treatable. However, once metastasis sets in, cancerous cells have invaded the body and while surgical resection may remove the parent tumor, this does not address other tumors. Only chemotherapy, or some particular form of targeting therapy, then stands any chance of success.

The process of tumor metastasis is a multistage event involving local invasion and destruction of the intracellular matrix, intravasation into blood vessels, lymphatics or other channels of transport, survival in the circulation, extravasation out of the vessels in the secondary site(s), and growth in the new location(s) (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Success in establishing metastatic deposits requires tumor cells to be able to accomplish these steps sequentially. Common to many steps of the metastatic process is a requirement for motility. The enhanced movement of malignant tumor cells is a major contributor to the progression of the disease toward metastasis. Increased cell motility has been associated with enhanced metastatic potential in animal as well as human tumors (Hosaka, et al., Gann 69, 273-276 (1978) and Haemmerlin, et al., Int. J. Cancer 27, 603-610 (1981)).

Tumor angiogenesis is essential for both primary tumor expansion and metastatic tumor spread (Blood et al., Biochim. Biophys. Acta 1032:89-118 (1990)). Angiogenesis is a fundamental process by which new blood vessels are formed. Progressive tumor growth necessitates the continuous induction of new capillary blood vessels which converge upon the tumor. In addition, the presence of blood vessels within a tumor provides a ready route for malignant cells to enter the blood stream and initiate metastasis. Thus, malignancy is a systemic disease in which interactions between the neoplastic cells and their environment play a crucial role during evolution of the pathological process (Fidler, I. J., Cancer Metastasis Rev. 5:29-49 (1986)).

Identifying factors that are associated with tumor progression, particularly metastasis and angiogenesis, is clearly a prerequisite not only for a full understanding of cancer, but also for the development of rational new anti-cancer therapies. In addition to using such factors for diagnosis and prognosis, these factors represent important targets for identifying novel anti-cancer compounds, and are useful for identifying new modes of treatment, such as inhibition of metastasis. One difficulty, however, is that the genes characteristic of cancerous cells are very often host genes being abnormally expressed. For example, a protein marker for a given cancer, while expressed in high levels in connection with that cancer, may also be expressed elsewhere throughout the body, albeit at reduced levels. Thus, some care is required in determining whether the expression of any single gene in a given cancer is a meaningful marker for the progression of the disease.

Although progress has been made in the identification of various potential breast cancer marker genes, as well as other biomolecular markers of cancer (e.g., Prostate Specific Antigen in the case of Prostate cancer) there remains a continuing need for new marker genes along with their expressed proteins that can be used to specifically and selectively identify the appearance and pathogenic development of cancer in a patient.

PCT publication WO 00/58473 discloses a sequence of Clone 3003. Clone 3003 contains two identifiable domains one of which is a collagen triple helix. The PCT publication reports that Clone 3003 is expressed in thyroid, bone marrow and lymph node and is believed to have disease associations related to hyper- and hypoparathyroidism, hemophilia, hypercoagulation, idiopathic thrombocytopenia purpura, autoimmune diseases, allergies, immunodeficiencies, transplantation complications, graft versus host disease and lymphedema. The PCT publication WO 00/58473 does not teach or disclose an association of this clone to cancer.

SUMMARY OF THE INVENTION

We have discovered a protein in humans, herein referred to as collagen like gene (CLG) product (SEQ ID NOS: 12 and 13), that is expressed in human prostate cancer and breast cancer cell lines but not in normal adult, placenta, lung, liver, skeletal muscle, kidney or pancreas tissues. We have also discovered that the level of CLG mRNA expression correlates positively with the metastatic potential of the cancer cell lines tested. We have also discovered an alternative form of CLG expressed in particular human heart tissues (SEQ ID NOS: 1 and 2). We have further discovered a related molecule expressed in rats (SEQ ID NOS: 3 and 4) and mice (SEQ ID NOS: 5 and 6).

These results indicate that increased expression of CLG has a high correlation to disease state in a number of cancers, including prostate and breast cancer, and is particularly associated with metastatic cancers. Accordingly, assaying for enhanced levels of transcript or gene product can be used not only in a diagnostic manner, but also in a prognostic manner for particular cancers. Additionally, CLG can be used alone or in conjunction with other cancer markers, e.g., PSA and thymosin β15, in the diagnosis and prognosis of cancer.

Accordingly, one aspect of the invention pertains to methods for detecting the presence of CLG in a biological sample. In a preferred embodiment, the method involves contacting a biological sample (e.g., a tissue or tumor sample or isolate of such a sample) with an agent capable of detecting CLG protein or nucleic acid (e.g., mRNA or cDNA) molecule such that the presence of CLG is detected in the biological sample. Preferably, the CLG comprises residues 111-540 of SEQ ID NO: 13 (extracellular domain).

The agent can be, for example, a labeled or labelable nucleic acid probe capable of hybridizing to a CLG nucleic acid molecule or a labeled or labelable antibody capable of binding to CLG protein.

The present invention further provides a method of diagnosing cancer, especially prostate cancer and breast cancer in a patient by measuring levels of CLG in a biological specimen obtained from the patient. Levels of CLG in the sample greater than a base line level for that type of specimen is indicative of cancer. Biological specimens include, for example, blood, tissue, serum, stool, urine, sputum, cerebrospinal fluid and supernatant from cell lysate. The determination of base lines and comparison levels is by standard modes of analysis based upon the present disclosure.

In another aspect, the present invention provides a method of prognosis in an individual having cancer, the method comprising:
  obtaining a biological specimen (e.g., tumor sample) from said individual;
  measuring CLG amounts to obtain a CLG level in said specimen; and
  correlating said CLG levels with a baseline level: levels higher than the baseline indicate an unfavorable prognosis and levels at or lower than the baseline indicate a favorable prognosis. CLG mRNA or protein may be measured to obtain CLG levels. Preferably, the CLG comprises residues 111-540 of SEQ ID NO: 13.

In yet another aspect, the present invention provides a method for determining the metastatic potential of a tumor by measuring the level of CLG expression in the tumor. Expression of CLG in said tumor greater than a base line level for that particular tissue indicates an increased metastatic potential.

In yet another embodiment, changes in condition can be monitored by comparing changes in CLG expression levels in the tumor in that subject over time.

In the methods of the present invention, levels of CLG can be ascertained by measuring the protein directly or indirectly by measuring mRNA transcript encoding CLG. mRNA levels can be measured, for example, using Northern blot analysis or an RNA dependent polymerase chain reaction, e.g., reverse transcriptase PCR (RT-PCR). DNA chip technology may also be used to measure mRNA levels.

Base line levels can be determined readily by measuring levels of CLG in samples of disease free individuals.

The present invention also provides a method for measuring CLG levels which comprises the steps of:
  contacting a biological specimen with an antibody or antibody fragment which selectively binds CLG, and
  detecting whether said antibody or said antibody fragment is bound by said sample and thereby measuring the levels of CLG.

In still another embodiment of this invention, the protein can serve as a target for agents that disrupt its function, inhibit its activity, or inhibit its expression. Such agents include compounds or antibodies that bind to CLG such that its function is inhibited. For example, one can add an effective amount of a compound that binds to CLG to disrupt function and thus inhibit metastasis. In another embodiment, one can use CLG expressing cells in an assay to discover compounds that bind to or otherwise interact with this protein in order to discover compounds that can be used to inhibit metastasis.

In a further embodiment of the invention, CLG or an immunogenic polypeptide thereof (or DNA encoding the protein or polypeptide) may be used in a pharmaceutical composition or vaccine to treat cancer or to inhibit the development of cancer.

The present invention provides isolated nucleic acids (polynucleotides) which encode CLG having the deduced amino acid sequence of SEQ ID. NO: 2, 4, 6 or 13 or a unique fragment thereof.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptides may be identical to the coding sequence shown in SEQ ID NOS: 1, 3, 5 or 12 or may be a different coding sequence which coding sequence, as a result of the redundancy or degeneracy of the genetic code, encodes the same protein as the DNA of SEQ ID NOS: 1, 3, 5 or 12.

The polynucleotide may have a coding sequence which is a naturally occurring allelic variant of the coding sequence shown in SEQ ID NOS: 1, 3, 5 or 12. As known in the art, an allelic variant is an alternate form of a polynucleotide sequence which may have a substitution, deletion or addition of one or more nucleotides, which does not substantially alter the function of the encoded protein.

The present invention also provides an isolated polynucleotide segment which hybridize under stringent conditions to a unique portion of the hereinabove-described polynucleotides, particularly SEQ ID NOS: 1, 3, 5 or 12. The segment preferably comprises at least 10 nucleotides. Most preferably, the isolated segment hybridizes to nucleotides 1-1511 of SEQ ID NO: 1 or nucleotides 1-1375 of SEQ ID NO: 12. As herein used, the term "stringent conditions" means hybridization will occur only if there is at least 95% and preferably at least 97% identity between the sequences. These isolated segments may be used in nucleic acid amplification techniques, e.g., PCR, to identify and/or isolate polynucleotides encoding CLG.

As used herein a polynucleotide "substantially identical" to SEQ ID NOS: 1, 3 or 12 is one comprising at least 90% identity, preferably at least 95% identity, most preferably 99% identity to SEQ ID NOS: 1, 3 or 12. The reason for this is that such a sequence can encode CLG in multiple mammalian species.

The present invention further provides an isolated and purified human CLG having the amino acid sequence of SEQ ID NO: 2 or 13 (or rat CLG SEQ ID NO: 4 or mouse CLG SEQ ID NO: 6), or a unique fragment thereof, as well as polypeptides comprising such unique fragments. Unique fragments include, for example, amino acids 1-386 of SEQ ID NO: 2, amino acids 438-457 of SEQ ID NO: 2, and 1-329 of SEQ ID NO: 4. A preferred fragment is amino acids 111-540 of SEQ ID NO: 13.

In accordance with yet another aspect of the present invention, there are provided isolated antibodies or antibody fragments which selectively bind human CLG. The antibody fragments include, for example, Fab, Fab', F(ab')2 or Fv fragments. The antibody may be a single chain antibody, a humanized antibody or a chimeric antibody.

The term "isolated" means that the material is removed from its original environment (e.g., the natural environment if it is naturally occurring). For example, naturally-occurring polynucleotides or polypeptides present in a living animal are not isolated, but the same polynucleotides or DNA or polypeptides, separated from some or all of the coexisting materials in the natural system, are isolated. Such polynucleotides could be part of a vector and/or such polynucleotides or polypeptides could be part of a composition, and still be isolated in that such vector or composition is not part of its natural environment.

As used herein, a "biological sample" or "biological specimen" refers to a sample of biological material obtained from a subject, preferably a human subject, or present within a subject, preferably a human subject, including a tissue, tissue sample, or cell sample (e.g., a tissue biopsy, for example, an aspiration biopsy, a brush biopsy, a surface biopsy, a needle biopsy, a punch biopsy, an excision biopsy, an open biobsy, an incision biopsy or an endoscopic biopsy), tumor, tumor sample, or biological fluid (e.g., blood, serum, lymph, spinal fluid).

As used herein, a "tissue sample" refers to a portion, piece, part, segment, or fraction of a tissue which is obtained or removed from an intact tissue of a subject, preferably a human subject. For example, tissue samples can be obtained from the pancreas, stomach, liver, secretory gland, bladder, lung, skin, prostate gland, breast ovary, cervix, uterus, brain, eye, connective tissue, bone, muscles or vasculature. In a preferred embodiment, the biological sample is a breast tissue sample. In another embodiment, the biological sample is a tissue sample, provided that it is not a breast tissue sample. In yet another embodiment, the biological sample is a tumor sample (e.g., a tumor biopsy).

As used herein, a "tumor sample" refers to a portion, piece, part, segment, or fraction of a tumor, for example, a tumor which is obtained or removed from a subject (e.g., removed or extracted from a tissue of a subject), preferably a human subject. A tumor sample can be obtained, for example, from a lung carcinoma, a colon carcinoma, a cervical carcinoma, an adenocarcinoma, a melanoma, a leukemia, a lymphoma, a glioma, a neuroblastoma, a retinoblastoma, and a sarcoma. In one embodiment, the tumor sample is obtained from a breast tumor (e.g., a breast tumor sample). In another embodiment, the tumor sample is obtained from a tumor, provided that the tumor is not a breast tumor. In yet another embodiment, the tumor sample is obtained from a primary tumor (e.g., is a primary tumor sample). In another embodiment, the biological sample is obtained metastatic lesion (e.g., is a metastatic lesion sample).

As defined herein, a "primary tumor" is a tumor appearing at a first site within the subject and can be distinguished from a "metastatic tumor" which appears in the body of the subject at a remote site from the primary tumor. As used herein, a "metastatic tumor" is a tumor resulting from the dissemination of cells from a primary tumor by the lymphatics or blood vessels or by direct extension through serumcontaning or serum-producing cavities or other spaces.

The present invention also encompasses the use of isolates of a biological sample in the methods of the invention. As used herein, an "isolate" of a biological sample (e.g., an isolate of a tissue or tumor sample) refers to a material or composition (e.g., a biological material or composition) which has been separated, derived, extracted, purified or isolated from the sample and preferably is substantially free of undesireable compositions and/or impurities or contaminants associated with the biological sample.

Preferred isolates include, but are not limited to, DNA (e.g., cDNA or genomic DNA), RNA (e.g., mRNA), and protein (i.e., purified protein, protein extracts, polypeptides).

Additional preferred isolates include cells as well as biological fluids (e.g., blood, serum, lymph, spinal fluid).

The present invention also relates to vectors which include polynucleotides of the present invention, host cells which are genetically engineered with vectors of the invention and the production of polypeptides of the invention by recombinant techniques.

The present invention further provides a method of treating a neoplastic cell expressing human CLG by administering to the cell an effective amount of a compound which suppresses the activity or production of the human CLG. Preferably, the compound interferes with the expression of the human CLG gene. Such compounds include, for example, antisense oligonucleotides, si RNAs, ribozymes, antibodies, including single chain antibodies and fragments thereof and aptamers.

Other aspects of the invention are disclosed infra.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

FIGS. 1A-1B is a nucleotide sequence of human CLG; SEQ ID NO: 1 and amino acid sequence, SEQ ID NO: 2.

FIG. 2A-2B is a nucleotide sequence of rat CLG; SEQ ID NO: 3 and amino acid sequence, SEQ ID NO: 4.

FIG. 3A-3B is a nucleotide sequence of mouse CLG; SEQ ID NO: 5 and amino acid sequence, SEQ ID NO: 6.

FIG. 4 is a nucleotide sequence comparing rat (SEQ ID NO: 7) and human (SEQ ID NO: 8) 5' untranslated region (UTR) and promoter sequence.

FIG. 6 is a summary table of human tumor cell lines found to express CLG by RT-PCR.

FIG. 7 compares the amino acid sequence of human (SEQ ID NO:2) and rat (SEQ ID NO: 4) CLG protein.

Figure 5:
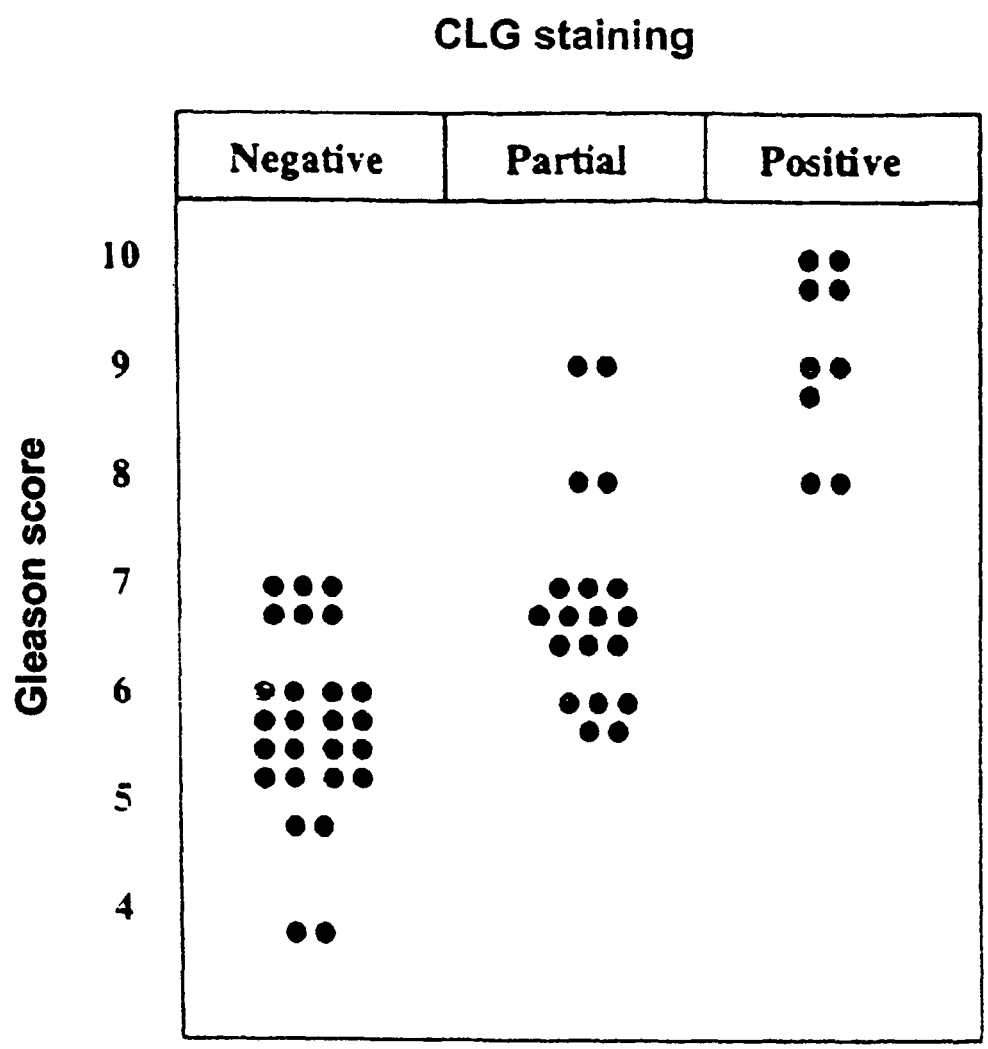
FIG. 5 is a correlation of CLG immunohistochemical staining with Gleason grade in human prostate tumors. Positive: homogenous staining with more than 50% of cell staining positively; Partial: heterogenous staining with 10-50% of cells showing positivity; Negative: less than 10% of cells showing positivity.

In the figure, collagenous domains are boxed. Transmembrane region is shaded. Epitopes of polyclonal chicken antibodies made are underlined.

NC1 domain (Extracellular side): AALEEERELLRRAGPP (SEQ ID NO: 9) Amino acid sequence following HNC1 epitope showed some similarity to other human receptor sequences thus were considered bad choices. As get closer to furin cleavage site, epitope would be cut by cleavage. Also preceded by RLLR sequence-chance that could be an alternative furin cleavage site.

Potential new epitope underlined (dotted line): DTVVIDYDGRILDALK (SEQ ID NO: 10).

Non-collagenous HNC4 epitope: KGESASDSLQESLAQLIVEP (SEQ ID NO:11)

C-terminal non-collagenous region: LDQPCPVGPDGLPVPGCWHK (SEQ ID NO: 14). High identity between transmembrane collagens XMII and XXV, therefore potentialy bad epitope.

FIG. 8A-8B is a nucleotide sequence of human CLG (short form); SEQ ID NO:12 and amino acid sequence, SEQ ID NO:13.

DETAILED DESCRIPTION OF THE INVENTION

We have discovered that collagen like gene (CLG) protein (SEQ ID NO:13) is associated with tumor metastases. We have shown that expression of CLG is upregulated in highly metastatic prostate cancer cell lines relative to poorly metastatic or nonmetastatic lines. Thus, expression of CLG can be used to determine metastatic potential. In addition, the protein provides a target for treatments to inhibit the metastatic process.

Accordingly, the evaluation and comparison of levels of mRNA transcript or protein, either normal or mutated, can be both diagnostic and prognostic for particular cancers. An elevated level, for example, is indicative of a greater tendency for metastatic activity, while lower levels indicate that the tumor has reduced metastatic potential. Further, by monitoring a particular neoplastic growth over a period of time and comparing changes in level one can evaluate changes in metastatic activity.

The present invention provides a method of diagnosing cancer, preferably prostate, or breast cancer, in a patient by measuring levels of CLG in a biological specimen/sample obtained from the patient Levels of CLG in the sample greater than a baseline level are indicative of cancer. Baseline levels can readily be determined by measuring levels of CLG in a sample of disease free individuals. Additionally, disease progression can be assessed by following CLG levels in individual patients over time.

The present invention also provides a method of prognosis in an individual having cancer, preferably pancreatic, prostate, leukemia and breast cancer, by measuring levels of CLG in a tumor sample or biological sample obtained from a patient to be tested. Expression of CLG in said tumor or biological sample greater than a base line level indicates a higher risk of tumor metastasis. This information can be used by the physician in determining the most effective course of treatment.

Changes in a patient's condition can be monitored using the methods of the present invention by comparing changes in CLG expression levels in the tumor in that subject over time.

The present invention further provides a method for determining the metastatic potential of a tumor by measuring the level of CLG expression in the tumor. Expression of CLG in said tumor greater than a base line level for that particular tissue indicates an increased metastatic potential.

CLG Detection Techniques

The present invention features agents which are capable of detecting CLG polypeptide or mRNA such that the presence of CLG is detected. As defined herein, an "agent" refers to a substance which is cabable of identifying or detecting CLG in a biological sample (e.g., identifies or detects CLG mRNA, CLG DNA, CLG protein, CLG activity). In one embodiment, the agent is a labeled or labelable antibody which specifically binds to CLG polypeptide. As used herein, the phrase "labeled or labelable" refers to the attaching or including of a label (e.g., a marker or indicator) or ability to attach or include include a label (e.g., a marker or indicator). Markers or indicators include, but are not limited to, for example, radioactive molecules, colorimetric molecules, and enzymatic molecules which produce detectable changes in a substrate.

In one embodiment the agent is an antibody which specifically binds to all or a portion of a CLG protein. As used herein, the phrase "specifically binds" refers to binding of, for example, an antibody to an epitope or antigen or antigenic determinant in such a manner that binding can be displaced or competed with a second preparation of identical or similar epitope, antigen or antigenic determinant. In an exemplary embodiment, the agent is an antibody which specifically binds to all or a portion of the human CLG protein.

In yet another embodiment the agent is a labeled or labelable nucleic acid probe capable of hybridizing to CLG mRNA. For example, the agent can be an oligonucleotide primer for the polymerase chain reaction which flank or lie within the nucleotide sequence encoding human CLG. In a preferred embodiment, the biological sample being tested is an isolate, for example, RNA. In yet another embodiment, the isolate (e.g., the RNA) is subjected to an amplification process which results in amplification of CLG nucleic acid. As defined herein, an "amplification process" is designed to strengthen, increase, or augment a molecule within the isolate. For example, where the isolate is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

CLG Nucleic Acid Probes

Types of probe include cDNA, riboprobes, synthetic oligonucleotides and genomic probes. The type of probe used will generally be dictated by the particular situation, such as riboprobes for in situ hybridization, and cDNA for Northern blotting, for example. Most preferably, the probe is directed to nucleotide regions unique to the protein. Detection of the CLG encoding gene, per se, will be useful in screening for mutations associated with enhanced expression. Other forms of assays to detect targets more readily associated with levels of expression—transcripts and other expression products—will generally be useful as well. The probes may be as short as is required to differentially recognize CLG mRNA transcripts, and may be as short as, for example, 15 bases; however, probes of at least 17 bases, more preferably 18 bases and still more preferably 20 bases are preferred.

A probe may also be reverse-engineered by one skilled in the art from the amino acid sequence of SEQ ID NOS: 2 or 13. However use of such probes may be more limited than the native DNA sequence, as it will be appreciated that any one given reverse-engineered sequence will not necessarily hybridize well, or at all, with any given complementary sequence reverse-engineered from the same peptide, owing to the degeneracy of the genetic code. This is a factor common in the calculations of those skilled in the art, and the degeneracy of any given sequence is frequently so broad as to yield a large number of probes for any one sequence.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

CLG RNA Detection Techniques

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography.

Detection of RNA transcripts can further be accomplished using known amplification methods. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994).

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; and target mediated amplification, as described by PCT Publication WO 9322461.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with haematoxylin to demonstrate the histological composition of the sample, and dark field imaging with a suitable light filter shows the developed emulsion. Non-radioactive labels such as digoxigenin may also be used.

CLG Antibodies

An isolated CLG protein, or fragment thereof, can be used as an immunogen to generate antibodies that bind CLG using standard techniques for polyclonal and monoclonal antibody preparation. The full-length CLG protein can be used or, alternatively, the invention provides antigenic peptide fragments of CLG for use as immunogens. The antigenic peptide of CLG comprises at least 8 amino acid residues of the amino acid sequence shown in SEQ ID NOS: 2 or 13 and encompasses an epitope of CLG such that an antibody raised against the peptide forms a specific immune complex with CLG. Preferred peptides include, for example, at least amino acids 66-81, 438-457 and 111-540 of SEQ ID NO 13. Preferably, the antigenic peptide comprises at least 10 amino acid residues, more preferably at least 15 amino acid residues, even more preferably at least 20 amino acid residues, and most preferably at least 30 amino acid residues. Antigenic polypeptides comprising at least 50, 100, 150, 200 or 250 amino acid residues are also within the scope of the present invention. Preferred epitopes encompassed by the antigenic peptide are regions of CLG that are located on the surface of the protein, e.g., hydrophilic regions. Additionally, preferred epitopes are non-collogenous regions. See, FIG. 8A-8B.

A CLG immunogen typically is used to prepare antibodies by immunizing a suitable subject, (e.g., rabbit, goat, mouse or other mammal) with the immunogen. An appropriate immunogenic preparation can contain, for examples, recombinantly expressed CLG protein or a chemically synthesized CLG peptide. The preparation can further include an adjuvant, such as Freund's complete or incomplete adjuvant, or similar immunostimulatory agent. Immunization of a suitable subject with an immunogenic CLG preparation induces a polyclonal anti-CLG antibody response. The immunogen can further include a portion of non-CLG polypeptide, for example, a polypeptide useful to facilitate purification.

Accordingly, another aspect of the invention pertains to anti-CLG antibodies.

The term "antibody" as used herein refers to immunoglobulin molecules and immunologically active portions of immunoglobulin molecules, i.e., molecules that contain an antigen binding site which specifically binds (immunoreacts with) an antigen, such as CLG. The invention provides polyclonal and monoclonal antibodies that bind CLG. The term "monoclonal antibody" or "monoclonal antibody composition", as used herein, refers to a population of antibody molecules that contain only one species of an antigen binding site capable of immunoreacting with a particular epitope of CLG. A monoclonal antibody composition thus typically displays a single binding affinity for a particular CLG protein with which it immunoreacts.

Polyclonal antibodies generated by the above technique may be used directly, or suitable antibody producing cells may be isolated from the animal and used to form a hybridoma by known means (Kohler and Milstein, Nature 256: 795. (1975)). Selection of an appropriate hybridoma will also be apparent to those skilled in the art, and the resulting antibody may be used in a suitable assay to identify CLG.

CLG Protein Detection Techniques

It is generally preferred to use antibodies, or antibody equivalents, to detect CLG protein. Methods for the detection of protein are well known to those skilled in the art, and include ELISA (enzyme linked immunosorbent assay), RIA (radioimmunoassay), Western blotting, and immunohistochemistry. Immunoassays such as ELISA or RIA, which can be extremely rapid, are more generally preferred.

Samples for diagnostic purposes may be obtained from any number of sources. A sample obtained directly from the tumor, such as the stroma or cytosol, may be used to determine the metastatic potential of the tumor. It may also be appropriate to obtain the sample from other biological specimens, such as blood, lymph nodes, or urine. Such diagnosis may be of particular importance in monitoring progress of a patient, such as after surgery to remove a tumor. If a reference reading is taken after the operation, then another taken at regular intervals, any rise could be indicative of a relapse, or possibly a metastasis.

ELISA and RIA procedures may be conducted such that a CLG standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, CLG in the sample is allowed to react with the corresponding immobilized antibody, radioisotope- or enzyme-labeled anti-CLG antibody is allowed to react with the system, and radioactivity or the enzyme assayed (ELISA-sandwich assay). Other conventional methods may also be employed as suitable.

The above techniques may be conducted essentially as a "one-step" or "two-step" assay. The "one-step" assay involves contacting antigen with immobilized antibody and, without washing, contacting the mixture with labeled antibody. The "two-step" assay involves washing before contacting the mixture with labeled antibody. Other conventional methods may also be employed as suitable.

Enzymatic and radiolabeling of CLG and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect CLG according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-CLG antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of human CLG in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

CLG Detection Kit

The invention also encompasses kits for detecting the presence of CLG in a biological sample (e.g., a tumor sample). For example, the kit can comprise a labeled or labelable agent capable of detecting CLG protein or mRNA in a biological sample and a means for determining the amount of CLG in the sample. The agent can be packaged in a suitable container. The kit can further comprise a means for comparing the amount of CLG in the sample with a standard and/or can further comprise instructions for using the kit to detect CLG mRNA or protein.

This invention provides a convenient kit for measuring human CLG. This kit includes antibodies or antibody fragments which selectively bind human CLG or a set of DNA oligonucleotide primers that allows synthesis of cDNA encoding the protein or a DNA probe that detects expression of CLG mRNA. Preferably, the primers and probes comprise at least 15, most preferably 17, nucleotides and hybridize under stringent conditions to a DNA fragment having the nucleotide sequence set forth in SEQ ID NOS: 1, 3 or 12. As herein used, the term "stringent conditions" means hybridization will occur only if there is at least 95% and preferably at least 97% identity between the sequences.

Methods of Detection

The invention provides a method for detecting the presence of CLG in a biological sample. The method involves contacting the biological sample with an agent capable of detecting CLG protein or nucleic acid molecules (e.g., CLG mRNA) such that the presence of CLG is detected in the biological sample. A preferred agent for detecting CLG mRNA is a labeled or labelable nucleic acid probe capable of hybridizing to CLG mRNA. The nucleic acid probe can be, for example, the full-length CLG cDNA of SEQ ID NOS: 1 or 12, or a portion thereof, such as an oligonucleotide of at least 15, 30, 50, 100, 250 or 500 nucleotides in length and sufficient to specifically hybridize under stringent conditions to CLG mRNA.

A preferred agent for detecting CLG protein is a labeled or labelable antibody capable of binding to CLG protein. Antibodies can be polyclonal, or more preferably, monoclonal. An intact antibody, or a fragment thereof (e.g., Fab or F (ab') 2) can be used.

The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

As used herein, the term "isolated", when used in the context of a biological sample, is intended to indicate that the biological sample has been removed from the subject. In one embodiment, a biological sample comprises a sample which has been isolated from a subject and is subjected to a method of the present invention without further processing or manipulation subsequent to its isolation. In another embodiment, the biological sample can be processed or manipulated subsequent to being isolated and prior to being subjected to a method of the invention. For example, a sample can be refrigerated (e.g., stored at 4° C.), frozen (e.g., stored at −20° C., stored at −135° C., frozen in liquid nitrogen, or cryopreserved using any one of many standard cryopreservation techniques known in the art). Furthermore, a sample can be purified subsequent to isolation from a subject and prior to subjecting it to a method of the present invention.

As used herein, the term "purified" when used in the context of a biological sample, is intended to indicate that at least one component of the isolated biological sample has been removed from the biological sample such that fewer components, and consequently, purer components, remain following purification. For example, a serum sample can be separated into one or more components using centrifugation techniques known in the art to obtain partially-purified sample preparation. Furthermore, it is possible to purify a biological sample such that substantially only one component remains. For example, a tissue or tumor sample can be purified such that substantially only the protein or mRNA component of the biological sample remains.

Furthermore, it may be desirable to amplify a component of a biological sample such that detection of the component is facilitated. For example, the mRNA component of a biological sample can be amplified (e.g., by RT-PCR) such that detection of CLG mRNA is facilitated. As used herein, the term "RT-PCR" (an abbreviation for reverse transcriptase-polymerase chain reaction) involves subjecting mRNA to the reverse transcriptase enzyme results in the production of cDNA which is complementary to the base sequences of the mRNA. Large amounts of selected cDNA can then be produced by means of the polymerase chain reaction which relies on the action of heat-stable DNA polymerase for its amplification action. Alternative amplification methods include: self sustained sequence replication (Guatelli, J. C. et al., 1990, Proc. Natl. Acad. Sci. USA 87: 1874-1878), transcriptional amplification system (Kwoh, D. Y. et al., 1989, Proc. Natl. Acad. Sci. USA 86: 1173-1177), Q-Beta Replicase (Lizardi, P. M. et all, 1988, Bio/Technology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

The detection methods of the present invention can be used to detect CLG protein or nucleic acid molecules in a biological sample in vitro as well as in vivo. For example, in vitro techniques for detection of CLG mRNA include Northern hybridizations and in situ hybridizations. In vitro techniques for detection of CLG DNA include Southern hybridizations. In vitro techniques for detection of CLG protein include enzyme linked immunosorbent assays (ELISAs), Western blots, immunoprecipitations and immunofluorescence. Alternatively, CLG protein can be detected in vivo in a subject by introducing into the subject a labeled anti-CLG antibody.

For example, the antibody can be labeled with a radioactive marker whose presence and location in a subject can be detected by standard imaging techniques.

In a preferred embodiment of the detection method, the biological sample is a tissue sample or tumor sample. The tissue sample or tumor sample may comprise tissue or a suspension of cells. A tissue section, for example, a freeze-dried, parafinembedded, or fresh frozen section of tissue removed from a patient, or a section of a tumor biopsy can be used as the biological sample. Moreover, the sample may include a biological fluid obtained from a subject (e.g., blood, ascites, pleural fluid or spinal fluid). Following collection, tissue or tumor samples can be stored at temperatures below −20° C. to prevent degradation until the detection method is to be performed. In one embodiment, a biological sample in which CLG mRNA or protein is to be detected is a mammary tumor sample. In another embodiment, a biological sample in which CLG mRNA is to be detected is, for example, a lung, colon, or cervical tumor.

The detection methods of the invention described above can be used as the basis for a method of diagnosis of a subject with a tumor (e.g., a breast tumor), can be used as the basis for a method of monitoring the progression of cancer in a subject, or can be used as the basis for a method of prognosing a person at risk for developing a cancer.

In one embodiment, the invention features a method of determining the metastatic potential of a tumor which involves contacting a sample of the tumor (or isolate) with an agent capable of detecting CLG polypeptide or mRNA such that the presence of CLG polypeptide or mRNA is detected in the tumor sample or isolate, thereby determining the metastatic potential of the tumor. Another aspect of the invention features a prognostic method for determining whether a subject is at risk for developing cancer which involves contacting a biological sample obtained from the subject (or isolate of the sample) with an agent capable of detecting CLG polypeptide or mRNA such that the presence of CLG polypeptide or mRNA is detected in the biological sample or isolate, thereby determining whether the subject is at risk for developing cancer. Yet another aspect of the invention features a method of diagnosing cancer in a subject which involves contacting a biological sample obtained from the subject (or isolate of the sample) with an agent capable of detecting CLG polypeptide or mRNA such that the presence of CLG polypeptide or mRNA is detected in the biological sample or isolate, thereby diagnosing cancer in the subject. In another embodiment, the diagnostic methods of the present invention further involve determining the level of CLG polypeptide or mRNA in the sample or isolate. In yet another embodiment, the diagnostic methods of the present invention involve comparing the level of CLG polypeptide or mRNA in the sample or isolate with the level of CLG polypeptide or mRNA in a control sample. In yet another embodiment, the diagnostic or prognostic methods further include the step of forming a prognosis or forming a diagnosis.

In one embodiment, the control is from normal cells and the tumor sample is a suspected primary tumor sample. Primary malignancy of the tumor cell sample can be diagnosed based on an increase in the level of expression of CLG mRNA or protein in the tumor sample as compared to the control. In another embodiment, the control is from normal cells or a primary tumor and the tumor sample is a suspected metastatic tumor sample. Acquisition of the metastatic phenotype by the suspected metastatic tumor sample can be diagnosed based on an increase in the level of CLG MARNA or protein in the tumor sample compared to the control.

CLG DNA and Protein Production

One aspect of the invention involves isolated nucleic acid molecules that encode CLG or biologically active portions thereof, as well as nucleic acid fragments sufficient for use as hybridization probes to identify CLG-encoding nucleic acid (e.g., CLG mRNA). As used herein, the term "nucleic acid molecule" is intended to include DNA molecules (e.g., cDNA or genomic DNA) and RNA molecules (e.g., mRNA). The nucleic acid molecule may be single-stranded or double-stranded, but preferably is double-stranded DNA. An "isolated" nucleic acid molecule is free of sequences which naturally flank the nucleic acid (i.e., sequences located at the 5' and 3' ends of the nucleic acid) in the genomic DNA of the organism from which the nucleic acid is derived. For example, in various embodiments, the isolated CLG nucleic acid molecule may contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a human mammary adenocarcinoma cell). Moreover, an "isolated" nucleic acid molecule, such as a cDNA molecule, may be free of other cellular material.

In a preferred embodiment, an isolated nucleic acid molecule of the invention comprises the nucleotide sequence shown in SEQ ID NO: 1. The sequence of SEQ ID NO: 1 corresponds to the human CLG cDNA (long form, containing exon 11). This cDNA comprises sequences encoding the CLG protein (i.e., "the coding region", from nucleotides 359 to 2116), and 3' untranslated sequences (nucleotides 2117 to 3202). Alternatively, the nucleic acid molecule may comprise only the coding region of SEQ ID NO: 1 (e.g., nucleotides 359-2116).

A particularly preferred portion of SEQ ID NO: 1 is nucleotides 1-1511 (or 1-1375 of SEQ ID NO:12). The invention further encompasses nucleic acid molecules that differ from SEQ ID NOS: 1 or 12 (and portions thereof) due to degeneracy of the genetic code and thus encode the same CLG protein as that encoded by SEQ ID NOS: 1 or 12. Accordingly, in another embodiment, an isolated nucleic acid molecule of the invention has a nucleotide sequence encoding a protein having an amino acid sequence shown in SEQ ID NOS: 2 or 13. Moreover, the invention encompasses nucleic acid molecules that encode biologically active portions of SEQ ID NOS: 2 or 13. A preferred portion is amino acids 111-585 of SEQ ID NO: 2 or amino acid 111-540.

A nucleic acid molecule having the nucleotide sequence of SEQ ID NOS: 1 or 12 (or SEQ ID NOS: 3 or 5), or a portion thereof, can be isolated using standard molecular biology techniques and the sequence information provided herin. For example, a human CLG cDNA library using all or portion of SEQ ID NOS: 1, 3 or 5 as a hybridization probe and standard hybridization techniques (e.g., as described in Sambrook, J., Fritsh, E. F., and Maniatis, T. *Molecular Cloning: A Laboratory Manual. 2nd., ed., Cold Spring Harbor Laboratory,* Cold Spring Harbor, N.Y., 1989). Moreover, a nucleic acid molecule encompassing all or a portion of SEQ ID NOS: 1, 3 or 5 can be isolated by the polymerase chain reaction using oligonucleotide primers designed based upon the sequence of SEQ ID NOS:1, 3 or 5. For example, mRNA can be isolated from mammary adenocarcinoma cells (e.g., by guanidinium-thiocyanate extraction procedure of Chirgwin et al. (1979) *Biochemistry* 18: 5294-5299) and cDNA can be prepared using reverse transcriptase (e.g Moloney MLV reverse transcriptase, available from Gibo/BRL, Bethesda, Md.; or AMV reverse transcriptase, available from Seikagaku America, Inc., St. Petersberg, Fla.). Synthetic oligonucleotide primers for PCR amplification can be designed based upon the nucleotide sequence shown in SEQ ID NOS: 1 or 12. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to CLG nucleotide sequence can be prepared by standard synthetic techniques, e.g., using an automated DNA synthesizer.

In addition to the human CLG nucleotide sequence shown in SEQ ID NOS: 1 or 12, it will be appreciated by those skilled in the art that DNA sequence polymorphisms that lead to changes in the amino acid sequences of CLG may exist within a population (e.g., the human population). Such genetic polymorphism in the CLG gene may exist among individuals within a population due to natural allelic variation. Such natural allelic variations can typically result in 1-5% variance in the nucleotide sequence of the a gene. Any and all such nucleotide variations and resulting amino acid polymorphisms in CLG that are the result of natural allelic variation and that do not alter the functional activity of CLG are intended to be within the scope of the invention. Moreover, nucleic acid molecules encoding CLG proteins from other species, and thus which have a nucleotide sequence which differs from the human sequence of SEQ ID NOS: 1 or 12, are intended to be within the scope of the invention. Nucleic acid molecules corresponding to natural allelic variants and non-human homologues of the human CLG cDNA of the invention can be isolated based on their homology to the human CLG nucleic acid disclosed herein using the human cDNA, or a portion thereof, as a hybridization probe-according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NOS: 1, 3, 5 or 12, nucleotides 1-1511 of SEQ ID NO:1 or nucleotides 1-1375 of SEQ ID NO:12. In other embodiment, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that at least sequences at least 65%, more preferably at least 70%, and even more preferably at least 75% homologous to each other typically remain hybridized to each other. Such stringent conditions are known to those skilled in the art and can be found in Current Protocols in Molecular Biology, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65 C. Preferably, an isolated nucleic acid molecule of the invention that hybridizes under stringent conditions to the sequence of SEQ ID NOS: 1, 3 or 5 correspond to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human CLG.

In addition to naturally-occurring allelic variants of the CLG sequence that may exist in the population, the skilled artisan will further appreciate that changes may be introduced by mutation into the nucleotide sequence of SEQ ID NOS: 1, 3 or 12 thereby leading to changes in the amino acid sequence of the encoded CLG protein, without altering the functional ability of the CLG protein. For example, nucleotide substitutions leading to amino acid substitutions at "non-essential" amino acid residues may be made in the sequence of SEQ ID NOS: 1, 3 or 12. A "non-essential" amino acid residue is a residue that can be altered from the wild-type sequence of CLG (e.g., the sequence of SEQ ID NO: 2) without altering the activity of CLG, whereas an "essential" amino acid residue is required for CLG activity.

Accordingly, another aspect of the invention pertains to nucleic acid molecules encoding CLG proteins that contain changes in amino acid residues that are not essential for CLG activity, e.g., residues that are not conserved or only semi-conserved among members of the subfamily. Such CLG proteins differ in amino acid sequence from SEQ ID NOS: 2 or 3 yet retain CLG activity. In one embodiment, the isolated nucleic acid molecule comprises a nucleotide sequence encoding a protein, wherein the protein comprises an amino acid sequence at least 60% homologous to the amino acid sequence of SEQ ID NOS: 2 or 13 and retains CLG activity. Preferably, the protein encoded by the nucleic acid molecule is at least 70% homologous to SEQ ID NOS: 2 or 13, more preferably at least 80% homologous to SEQ ID NOS: 2 or 13, even more preferably at least 90% homologous to SEQ ID NOS: 2 or 13, and most preferably at least 95% homologous to SEQ ID NOS: 2 or 13.

To determine the percent homology of two amino acid sequences (e.g., SEQ ID NOS: 2 or 13 and a mutant form thereof), the sequences are aligned for optimal comparison purposes (e.g., gaps may be introduced in the sequence of one protein for optimal alignment with the other protein). The amino acid residues at corresponding amino acid positions are then compared. When a position in one sequence (e.g., SEQ ID NOS: 2 or 13) is occupied by the same amino acid residue as the corresponding position in the other sequence (e.g., a mutant form of CLG), then the molecules are homologous at that position (i.e., as used herein amino acid "homology" is equivalent to amino acid "identity"). The percent homology between the two sequences is a function of the number of identical positions shared by the sequences (i.e., % homology=# of identical positions/total # of positions x 100). Such an alignment can be performed using any one of a number of computer algorithms designed for such a purpose. A preferred, non-limiting example of a mathematical algorithim utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

An isolated nucleic acid molecule encoding a CLG protein homologous to the protein of SEQ ID NOS: 2 or 13 can be created by introducing one or more nucleotide substitutions, additions or deletions into the nucleotide sequence of SEQ ID NOS: 1 or 12 such that one or more amino acid substitutions, additions or deletions are introduced into the encoded protein. Mutations can be introduced into SEQ ID NOS: 1 or 12 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in CLG is preferably replaced with another amino acid residue from the same side chain family. Alternatively, in another embodiment, mutations can be introduced randomly along all or part of a CLG coding sequence, such as by saturation mutagenesis, and the resultant mutants can be screened for CLG activity to identify mutants that retain CLG activity. Following mutagenesis of SEQ ID NOS: 1 or 12, the encoded protein can be expressed recombinantly and the CLG activity of the protein can be determined.

DNA encoding CLG and recombinant CLG may be produced according to the methods known in the art.

Recombinant methods are preferably used to produce the CLG protein. A wide variety of molecular and biochemical methods are available for generating and expressing the CLG; see e.g. the procedures disclosed in Molecular Cloning, A Laboratory Manual (2nd Ed., Sambrook, Fritsch and Maniatis, Cold Spring Harbor), Current Protocols in Molecular Biology (Eds. Ausubel, Brent, Kingston, More, Feidman, Smith and Stuhl, Greene Publ. Assoc., Wiley-Interscience, NY, N.Y. 1992) or other procedures that are otherwise known in the art.

CLG Cloning

Where it is desired to express the protein or a fragment thereof, any suitable system can be used. The general nature of suitable vectors, expression vectors and constructions therefor will be apparent to those skilled in the art.

Suitable expression vectors may be based on phages or plasmids, both of which are generally host-specific, although these can often be engineered for other hosts. Other suitable vectors include cosmids and retroviruses, and any other vehicles, which may or may not be specific for a given system. Control sequences, such as recognition, promoter, operator, inducer, terminator and other sequences essential and/or useful in the regulation of expression, will be readily apparent to those skilled in the art.

Correct preparation of nucleotide sequences may be confirmed, for example, by the method of Sanger et al. (Proc. Natl. Acad. Sci. USA 74:5463-7 (1977)).

A DNA fragment encoding the CLG or a fragment thereof, may readily be inserted into a suitable vector. Ideally, the receiving vector has suitable restriction sites for ease of insertion, but blunt-end ligation, for example, may also be used, although this may lead to uncertainty over reading frame and direction of insertion. In such an instance, it is a matter of course to test transformants for expression, 1 in 6 of which should have the correct reading frame. Suitable vectors may be selected as a matter of course by those skilled in the art according to the expression system desired.

CLG Protein Production

Isolated CLG protein and fragments thereof may be produced using any expression system known to those skilled in the art. Such suitable expression systems include bacteria, such as *E. coli*, and eukaryotes, such as yeast, baculovirus, insect or mammalian cell-based expression systems, etc., depending on the size, nature and quantity of the polypeptide.

The term "isolated" means that the polypeptide is removed from its original environment. For example, a naturally-occurring polynucleotide or polypeptide present in a living animal is not isolated, but the same polynucleotide or DNA or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

By transforming a suitable bacterial or eukaryotic organism, and preferably, a eukaryotic cell line, such as HeLa cells, with the plasmid obtained, selecting the eukaryotic transformant with geneticin, zeocin, blasticin or a similar compound (or ampicillin in the case of a bacterial transformant) or by other suitable means if required, and adding tryptophan or other suitable promoter-inducer if necessary, the desired polypeptide or protein may be expressed. The extent of expression may be analyzed by SDS polyacrylamide gel electrophoresis-SDS-PAGE (Laemelli, Nature 227:680-685 (1970)).

Suitable methods for growing and transforming cultures are usefully illustrated in, for example, Maniatis (Molecular Cloning, A Laboratory Notebook, Maniatis et al. (eds.), Cold Spring Harbor Labs, N.Y. (1989)).

Cultures useful for production of polypeptides or proteins may suitably be cultures of any living cells, and may vary from prokaryotic expression systems up to eukaryotic expression systems. One preferred prokaryotic system is that of *E. coli*, owing to its ease of manipulation. However, it is also possible to use a higher system, such as a mammalian cell line, for expression of a eukaryotic protein. Currently preferred cell lines for transient expression are the HeLa and Cos cell lines. Other expression systems include the Chinese Hamster Ovary (CHO) cell line and the baculovirus system.

Other expression systems which may be employed include streptomycetes, for example, and yeasts, such as *Saccharomyces* spp., especially *S. cerevisiae*. Any system may be used as desired, generally depending on what is required by the operator. Suitable systems may also be used to amplify the genetic material, but it is generally convenient to use *E. coli* for this purpose when only proliferation of the DNA is required.

The polypeptides and proteins may be isolated from the fermentation or cell culture and purified using any of a variety of conventional methods including: liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention.

Therapeutic Applications Using CLG

The presence of CLG protein is positively correlated with metastasis. Therefore, CLG protein could be useful in therapeutic and diagnostic applications. For example, therapeutic approaches include the use of antibodies to block CLG protein, the use of antibodies for imaging applications, antisense technology to block CLG expression, membrane localization for tumor targeting and delivery of therapeutics to tumor cells, and immunotherapies such as vaccines. Diagnostically, the cleavage of ectodomain of the CLG protein, easily detected in the blood serum or urine, can be used as a marker for metastic cancer.

CLG Blocking Antibodies or Aptamers

One can treat a range of afflictions or diseases associated with expression of the protein by directly blocking the protein. This can be accomplished by a range of different approaches, including the use of antibodies, small molecules, and antagonists. One preferred approach is the use of antibodies that specifically block activity of the protein. Aptemers may also be used.

In accordance with yet another aspect of the present invention, there are provided isolated antibodies or antibody fragments which selectively bind the protein. The antibody fragments include, for example, Fab, Fab', F(ab')2 or Fv fragments. The antibody may be a single chain antibody, a humanized antibody or a chimeric antibody.

Antibodies, or their equivalents, or other CLG antagonists may also be used in accordance with the present invention for the treatment or prophylaxis of cancers. Administration of a suitable dose of the antibody or the antagonist may serve to block the activity of the protein and this may provide a crucial time window in which to treat the malignant growth.

Prophylaxis may be appropriate even at very early stages of the disease, as it is not known what specific event actually triggers metastasis in any given case. Thus administration of the antibodies, their equivalents, intrabodies, antagonists which interfere with protein activity, may be effected as soon as cancer is diagnosed, and treatment continued for as long as is necessary, preferably until the threat of the disease has been removed. Such treatment may also be used prophylactically in individuals at high risk for development of certain cancers, e.g., prostate or breast.

A method of treatment involves attachment of a suitable toxin to the antibodies which then target the area of the tumor. Such toxins are well known in the art, and may comprise toxic radioisotopes, heavy metals, enzymes and complement activators, as well as such natural toxins as ricin which are capable of acting at the level of only one or two molecules per cell. It may also be possible to use such a technique to deliver localized doses of suitable physiologically active compounds, which may be used, for example, to treat cancers.

It will be appreciated that antibodies for use in accordance with the present invention, whether for diagnostic or therapeutic applications, may be monoclonal or polyclonal as appropriate. Antibody equivalents of these may comprise: the Fab' fragments of the antibodies, such as Fab, Fab', F(ab')2 and Fv; idiotopes; or the results of allotope grafting (where the recognition region of an animal antibody is grafted into the appropriate region of a human antibody to avoid an immune response in the patient), for example. Single chain antibodies may also be used. Other suitable modifications and/or agents will be apparent to those skilled in the art.

Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., Proc. Natl. Acad. Sci. U.S.A. 81,6851 (−1985); Takeda, et al., Nature 314, 452(1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additionally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain.

In addition to using antibodies to inhibit CLG, it may also be possible to use other forms of inhibitors. For example, it may be possible to identify antgonists that functionally inhibit CLG. In addition, it may also be possible to interfere with the binding of CLG to target proteins, Other suitable inhibitors will be apparent to the skilled person.

The present invention further provides use of the CLG for intracellular or extracellular targets to affect activity. Intracellular targeting can be accomplished through the use of intracellularly expressed antibodies referred to as intrabodies.

The antibody (or other inhibitors or intrabody) can be administered by a number of methods. One preferred method is set forth by Marasco and Haseltine in PCT WO94/02610, which is incorporated herein by reference. This method discloses the intracellular delivery of a gene encoding the antibody. One would preferably use a gene encoding a single chain antibody. The antibody would preferably contain a nuclear localization sequence. One preferably uses an SV40 nuclear localization signal. By this method one can intracellularly express an antibody, which can block CLG functioning in desired cells.

Where the present invention provides for the administration of, for example, antibodies to a patient, then this may be by any suitable route. If the tumor is still thought to be, or diagnosed as, localized, then an appropriate method of administration may be by injection direct to the site. Administration may also be by injection, including subcutaneous, intramuscular, intravenous and intradermal injections.

Aptamer can be produced using the methodology disclosed in a U.S. Pat. No. 5,270,163 and WO 91/19813.

Formulations may be any that are appropriate to the route of administration, and will be apparent to those skilled in the art. The formulations may contain a suitable carrier, such as saline, and may also comprise bulking agents, other medicinal preparations, adjuvants and any other suitable pharmaceutical ingredients. Catheters are one preferred mode of administration.

Imaging Techniques

Anti-CLG antibodies may also be used for imaging purposes, for example, to detect tumor metastasis. Suitable labels include radioisotopes, iodine ($^{125}$I, $^{121}$I), carbon ($^{14}$C), sulphur ($^{35}$S), tritium ($^{3}$H), indium ($^{112}$In), and technetium ($^{99m}$Tc), fluorescent labels, such as fluorescein and rhodamine, and biotin.

However, for in vivo imaging purposes, the position becomes more restrictive, as antibodies are not detectable, as such, from outside the body, and so must be labelled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the patient, such as barium or caesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99m. The labeled antibody or antibody fragment will then preferentially accumulate at the location of cells which contain CLG. The labeled antibody or antibody fragment can then be detected using known techniques.

Antisense Technology

CLG expression may also be inhibited in vivo by the use of antisense technology. Gene expression can be controlled through triple-helix formation or antisense DNA or RNA, both of which methods are based on binding of a polynucleotide to DNA or RNA. An antisense nucleic acid molecule which is complementary to a nucleic acid molecule encoding CLG can be designed based upon the isolated nucleic acid molecules encoding CLG. An antisense nucleic acid molecule can comprise a nucleotide sequence which is complementary to a coding strand of a nucleic acid, e.g. complementary to an mRNA sequence, constructed according to the rules of Watson and Crick base pairing, and can hydrogen bond to the coding strand of the nucleic acid. The antisense sequence complementary to a sequence of an mRNA can be complementary to a sequence in the coding region of the mRNA or can be complementary to a 5' or 3' untranslated region of the mRNA. Furthermore, an antisense nucleic acid can be complementary in sequence to a regulatory region of the gene encoding the mRNA, for instance a transcription initiation sequence or regulatory element. Preferably, an antisense nucleic acid complementary to a region preceding or spanning the initiation codon or in the 3' untranslated region of an mRNA is used. An antisense nucleic acid can be designed based upon the nucleotide sequence shown in SEQ ID NOS: 1 or 12. A nucleic acid is designed which has a sequence complementary to a sequence of the coding or untranslated region of the shown nucleic acid. Alternatively, an antisense nucleic acid can be designed based upon sequences of the CLG gene, which can be identified by screening a genomic DNA library with an isolated nucleic acid of the invention. For example, the sequence of an important regulatory element can be determined by standard techniques and a sequence which is antisense to the regulatory element can be designed.

The antisense nucleic acids and oligonucleotides of the invention can be constructed using chemical synthesis and enzymatic ligation reactions using procedures known in the art. The antisense nucleic acid or oligonucleotide can be chemically synthesized using naturally occurring nucleotides or variously modified nucleotides designed to increase the biological stability of the molecules or to increase the physical stability of the duplex formed between the antisense and sense nucleic acids e.g. phosphorothioate derivatives and acridine substituted nucleotides can be used. Alternatively, the antisense nucleic acids and oligonucleotides can be produced biologically using an expression vector into which a nucleic acid has been subcloned in an antisense orientation (i.e. nucleic acid transcribed from the inserted nucleic acid will be of an antisense orientation to a target nucleic acid of interest). The antisense expression vector is introduced into cells in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1 (1)1986.

In addition, ribozymes can be used to inhibit in vitro expression of CLG. For example, the nucleic acids of the invention can further be used to design ribozymes which are capable of cleaving a single-stranded nucleic acid encoding a CLG protein, such as a CLG mRNA transcript. A catalytic RNA (ribozyme) having ribonuclease activity can be designed which has specificity for an mRNA encoding CLG based upon the sequence of a nucleic acid of the invention (e.g., SEQ ID NO: 1). For example, a derivative of a Tetrahymena L-19 IVS RNA can be constructed in which the base sequence of the active site is complementary to the base sequence to be cleaved in a CLG-encoding mRNA. See for example Cech, et al., U.S. Pat. No. 4,987,071; Cech, et al., U.S. Pat. No. 5,116,742. Alternatively, a nucleic acid of the invention could be used to select a catalytic RNA having a specific ribonuclease activity from a pool of RNA molecules. See for example Bartel, D. and Szostak, J. W. Science 261: 1411-1418 (1993). RNA-mediated interference (RNAi) (Fire, et al., Nature 391: 806-811, 1998) may also be used.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

The antibodies, nucleic acids or antagonists of the invention are administered orally, topically, or by parenteral means, including subcutaneous and intramuscular injection, implantation of sustained release depots, intravenous injection, intranasal administration, and the like. Accordingly, antibodies or nucleic acids of the invention may be administered as a pharmaceutical composition comprising the antibody or nucleic acid of the invention in combination with a pharmaceutically acceptable carrier. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol Registered™, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene Registered™(Marion), Aquaphor Registered™ (Duke Laboratories), and the like. Other topical formulations include aerosols, bandages, and other wound dressings. Alternatively one may incorporate or encapsulate the compounds in a suitable polymer matrix or membrane, thus providing a sustained-release delivery device suitable for implantation near the site to be treated locally. Other devices include indwelling catheters and devices such as the Alzet Registered™ minipump. Ophthalmic preparations may be formulated using commercially available vehicles such as Sorbicare Registered™ (Allergan), Neodecadron Registered™ (Merck, Sharp & Dohme), Lacrilube Registered™, and the like, or may employ topical preparations such as that described in U.S. Pat. No. 5,124,155, incorporated herein by reference. Further, one may provide an antagonist in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The amount of antibody, nucleic acid or inhibitor required to treat any particular disorder will of course vary depending upon the nature and severity of the disorder, the age and condition of the subject, and other factors readily determined by one of ordinary skill in the art.

RNAi

RNAi has shown to be a powerful tool for manipulating gene expression in cells (Hannon, Nature 418:244-251, 2002). The technology arose from the observation that exogenous double-stranded RNAs induce gene silencing in plants and *Caenorhabditis elegans*. These double-stranded RNAs are processed into small interfering RNAs (siRNAs), which are incorporated into a conserved cellular machinery that mediates the suppression of homologous genes. Recently, small non-coding RNAs have been identified that can act as endogenous regulators of gene expression. These microRNAs typically form stem-loop structures, essentially short double-stranded RNAs, that enter the RNAi pathway (Knight et al., Science 293:2269-2271, 2001; Ketting et al., Genes Dev, 15:2654-2659, 2001; Hutvagner et al., Science 293:834-838, 2001; Grishok, et al., Cell 106:23-34, 2001). shRNAs, modeled after microRNAs, can be expressed from viral vectors to induce stable suppression of gene expression in cultured mammalian cells (Paddison and Hannon, Cancer Cell 2:17-23,2002). Methods for preparing interference RNAs are presented in detail in, for example, the US Patent Application No. 20020162126, which is herein incorporated by reference.

Immunotherapy

In further aspects, the present invention provides methods for using CLG or an immunoreactive polypeptide thereof (or DNA encoding the protein or polypeptides) for immunotherapy of cancer in a patient, preferably prostate cancer. As used herein, a "patient" refers to any warm-blooded animal, preferably a human. A patient may be afflicted with a disease, or may be free of detectable disease. Accordingly, CLG or an immunoreactive polypeptide thereof may be used to treat cancer or to inhibit the development of cancer.

In accordance with this method, the protein, polypeptide or DNA is generally present within a pharmaceutical composition and/or a vaccine. Pharmaceutical compositions may comprise the full length protein or one or more immunogenic polypeptides, and a physiologically acceptable carrier. The vaccines may comprise the full length protein or one or more immunogenic polypeptides and a non-specific immune response enhancer, such as an adjuvant, biodegradable microsphere (PLG) or a liposome (into which the polypeptide is incorporated).

Alternatively, a pharmaceutical composition or vaccine may contain DNA encoding CLG or an immunogenic polypeptide thereof, such that the full length protein or polypeptide is generated in situ. In such pharmaceutical compositions and vaccines, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter). Bacterial delivery systems involve the administration of a bacterium (such as Bacillus-Calmette-Guenin) that expresses an epitope of a prostate cell antigen on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., PNAS 86:317-321, 1989; Flexner et al., Ann. N.Y. Acad. Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, iotechniques 6:616-627, 1988; Rosenfeld et al., Science 252:431-434, 1991; Kolls et al., PNAS 91:215-219, 1994; Kass-Eisler et al., PNAS 90:11498-11502, 1993; Guzman et al., Circulation 88:2838-2848, 1993; and Guzman et al., Cir. Res. 73:1202-1207, 1993. Techniques for incorporating DNA into such expression systems are well known to those of ordinary skill in the art. The DNA may also be "naked," as described, for example, in published PCT application WO 90/11092, and Ulmer et al., Science 259:1745-1749 (1993), reviewed by Cohen, Science 259:1691-1692 (1993).

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3-24 week period. Preferably, 4 doses are administered, at an interval of 3 months, and booster administrations may be given periodically thereafter. Alternate protocols may be appropriate for individual patients. A suitable dose is an amount of polypeptide or DNA that is effective to raise an immune response (cellular and/or humoral) against tumor cells, e.g., prostate tumor cells, in a treated patient. A suitable immune response is at least 10-50% above the basal (i.e. untreated) level. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.01 mL to about 5 ml.

CLG or an immunogenic polypeptide thereof can be used in cell based immunotherapies, i.e. stimulation of dendritic cells with CLG or fusion with CLG expressing cells. The modified dendritic cells, once injected into the patient, are a cellular vaccine, where the dendritic cells activate an immune response against the CLG expressing cancer.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polyleptic galactide) may also be employed as carriers for the pharmaceutical compositions of this invention. Suitable biodegradable microspheres are disclosed, for example, in U.S. Pat. Nos. 4,897,268 and 5,075,109.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, Bordella pertussis or *Mycobacterium tuberculosis*. Such adjuvants are commercially available as, for example. Freund's Incomplete Adjuvant and Complete Adjuvant (Difco Laboratories. Detroit, Mich.) and Merck Adjuvant 65 (Merck and Company, Inc., Rahway, N.J.).

All references cited above or below are herein incorporated by reference.

The present invention is further illustrated by the following Examples. These Examples are provided to aid in the understanding of the invention and are not construed as a limitation thereof.

EXAMPLE 1

To search for genes involved in tumor metastasis, we compared gene expression between the well-characterized Dunning 3327 rat prostatic adenocarcinoma low-metastatic subline AT2.1 and high-metastatic AT6.1 using the differential mRNA display technique. We isolated a cDNA fragment representing mRNA that was expressed in the high-metastatic subline, AT6.1, but not in another high-metastatic subline AT3.1, nor in the low-metastatic subline AT2.1. The expression pattern shown by differential display was confirmed by RT-PCR and Western blot analysis.

In order to isolate the full-length cDNA of this gene, the cDNA fragment obtained from the differential display was used as a probe to screen an AT6.1 λgt10 cDNA library. Two positive clones were obtained, which contained 5'-end truncated sequences. To recover the missing sequence of the 5'-end of the cDNA, we used Rapid Amplification of cDNA Ends (RACE) PCR method. The 5'end was completed by the PCR based method of Rat Genome Walking in which 2.5 kb of genomic sequence upstream of the known cDNA was isolated and sequenced. A transcriptional start site was determined from AT6.1 RNA by the PCR based method of Inverse RACE. The 5'-untranslated region (UTR) was determined to consist of a 128 bp sequence ahead of the methionine translation start site in AT6.1 prostatic carcinoma RNA. We have determined that the AT6.1 rat prostatic carcinoma CLG transcript consists of 2733 bp, with a 1599 bp open reading frame. The 5' end of human CLG was determined from the human genome database, and we have to date amplified 358 bp of cDNA upstream of the predicted translational start site. We are currently determining whether this represents the complete 5' UTR, in which case the human sequence shown in FIGS. 1A-1B would represent the entire human CLG transcript. FIG. 4 demonstrates that a region of sequence upstream of the translation start site is identical in both the rat and human CLG gene. This homologous 117 bp sequence lies within the predicted 5'UTR of the human sequence and contains both identified 5'UTR and additional sequence in the rat CLG gene. This additional sequence may represent additional 5'UTR due to upstream transcriptional start sites. Multiple transcriptional strart sites have been identified in other transmembrane collagens. This identity suggests that this region of sequence may be an important regulatory site for transcriptional control of CLG expression. These sequences shown are likely to contain at least some of the core promoter elements of the CLG gene. BLAST searches against the NCBI database indicated that the human or rat RNA sequences listed herein were not identical to any identified gene and therefore CLG is a novel gene sequence.

The length of the human open reading frame is 1758 bp from the predicted translational start site, and the translated human and rat proteins show 91% homology as assessed by the Jotun Hein method. It can be seen that the rat CLG protein is smaller than the human CLG protein. This appears to be largely due to alternative splicing as the non-collagenous region NCII is removed in the AT6.1 RNA, joining the collagenous regions COL-1 and COL-2. We have also observed splice variants in human CLG transcripts, therefore the protein made may be variable. The deduced amino acid sequence contains a typical collagen Gly-X-Y pattern, in which every third residue is a glycine. Toward the amino-terminal end of the protein is a hydrophobic region of amino acids predictive of a transmembrane domain, according to analysis by TMHMM (transmembrane helix by hidden Markov model) and DAS (Dense Alignment Surface algorithm) transmembrane prediction programs. Thus the CLG protein is predicted to be a type II transmembrane collagen. The rat or human CLG sequence does not show high homology to any known collagens, except in the small most amino-terminal non-collagenous 20 amino acid region, NC-5, which shows 75% identity to collagen XIII, one of two previously identified transmembrane collagens. The function of this region is currently uncharacterized.

We have demonstrated localization of CLG in the cell membrane by immunoflorescent staining. Cells overexpressing the protein following transfection of either full length rat CLG or a truncated form of CLG, were stained with antibody AB 6.1 B (detailed below), and detected by anti-rabbit Texas Red-conjugated secondary antibody. Full length CLG was detected when cells were not permeabilized (i.e. the cells are not treated with detergent to allow the antibody access to the intracellular compartment) demonstrating that the protein is located on the cell membrane. The truncated form of rat CLG, aa 49-532 (missing most of the transmembrane domain, and the entire cytoplasmic amino-terminal end of the protein) was not detected in non-permeabilized cells and therefore not transported to the membrane. Membrane localization of overexpressed CLG was confirmed by membrane purification via temperature-induced separation of the hydrophilic and hydrophobic membrane compartments.

The tissue distribution of CLG mRNA was examined in major organs of the rat by Northern hybridization. No expression of CLG was detected in the heart, brain, lung, liver, skeletal muscle, spleen and kidney, whereas expression was detected in the testis. In human tissue, Northern hybridization demonstrated some expression in heart, and lower expression in brain, but no expression in lung, liver, kidney, pancreas, placenta or skeletal muscle. Even within the heart, Northern dot blot analysis shows that expression is limited to particular structures, namely, the interventricular septum, apex and right ventricle. Thus, CLG appears to show a very limited expression pattern.

We made a GST-fusion protein containing 108 amino acid residues from the C-terminus of the CLG protein and prepared a polyclonal antibody (AB 6.1B) to the fusion protein. This antibody was used for immunohistochemistry on human prostate cancer. Normal prostate epithelium showed no CLG expression. Heterogenous staining was observed in moderately differentiated prostate tumor, while strong staining was observed in poorly differentiated and invasive prostate cancer cells. The results show a general correlation between the expression of CLG protein and the Gleason grade with high-grade tumors (Gleason 8-10) showing a high percentage of positive staining compared to low-grade (Gleason 4-5) tumors (FIG. 5). This evidence suggests that CLG could be a useful marker for prognosis of human prostate cancer. Additionally this factor may be useful for imaging human tumors. We have also shown that CLG expression can be detected by Western Blot analysis. CLG protein expression is observed in the metastatic AT6.1 cells, but not in low metastatic AT2.1 cells, consistent with differential display and RT-PCR results. Upregulated expression of CLG was also observed in metastatic sublines of the human prostate carcinoma cell line PC-3 cell line series, by RT-PCR. Differential expression was further examined by RT-PCR on other tumor cell lines with various metastatic potential. Human breast carcinoma MDA-MB435, human colon carcinoma cell line HT29, human pancreatic carcinoma AsPC-1, and human leukemia cell lines K562 and HL60 all show upregulated expression of CLG. These studies indicate that the expression of CLG is not limited to prostate cancer, but is overexpressed in other types of cancer. The results suggest that CLG expression may also be associated with the metastatic process of other cancers and would be useful for diagnosis or prognosis. Antagonists of this factor may be effective therapeutic agents for prostatic cancer and other cancers. Because CLG is found on the cancer cell surface, it would be a useful target for vaccine generation or other forms of immunotherapy.

We have determined that the CLG protein can be cleaved and released from the cell surface. This processing of CLG would allow detection in bodily fluids, e.g. serum or urine. A potential cleavage motif of the Furin proprotein convertase family, enzymes also known as secretases or sheddases, exists in the amino acid sequence of the extracellular region of the NC-1 (non-collagenous domain-1). The size of the protein detected in the cell media is consistent with cleavage in this domain. We have also shown that chemical inhibition of furin cleavage results in decreased CLG cleavage and that furin-deficient cells cannot shed CLG from the cell surface.

We have also shown that capillary endothelial cells, which do not show CLG expression under normal conditions, can be induced to express CLG upon stimulation with the angiogenic growth factors bFGF or VEGF. CLG expression is upregulated in a time dependent manner. This expression is transient, and is downregulated within 12 hours. This suggests that CLG may play a role in angiogenic response and may be a potential target for anti-angiogenic therapy.

We have detected the presence of exon 11 in normal human heart cDNA, but not in human tumor cell lines i.e. K562 leukemia or HL60 leukemia cells. Detection of this splice variant could distinguish between "normal" CLG and tumor CLG. This could be done by RT-PCR on RNA samples, or by the use of antibodies that specifically recognize an epitope to the amino acid sequence formed by the splicing together of exons 10 and 12. This may be used as a diagnostic to detect an alternatively spliced domain.

The references cited throughout the specification are incorporated herein by reference. The present invention has been described with reference to specific embodiments. However, this application is intended to cover those changes and substitutions that may be made by those skilled in the art, without departing from the spirit and the scope of the appended claims.

What is claimed is:

1. A method for detecting the presence of cancer in a biological sample obtained from a subject, the method comprising contacting the biological sample with an antibody that binds CLG polypeptide of SEQ ID NO: 2 or SEQ ID NO: 13 such that the presence of CLG in the biological sample above baseline levels is indicative of cancer, wherein the cancer is prostate cancer or breast cancer.

2. The method of claim 1, wherein the biological sample is a prostate or breast tissue sample, or isolate thereof.

3. The method of claim 1, wherein the biological sample is a tumor sample, or isolate thereof.

4. The method of claim 3, wherein the tumor sample is a prostate or breast tumor sample.

5. The method of claim 1, wherein the biological sample is a primary tumor sample, or isolate thereof.

6. The method of claim 1, wherein the biological sample is a metastatic breast or a metastatic prostate lesion sample, or isolate thereof.

7. The method of claim 1, wherein the antibody is a labeled or labelable antibody which specifically binds to CLG polypeptide.

8. The method of claim 7, wherein the antibody specifically binds to a polypeptide selected from the group consisting of:
(a) a polypeptide comprising all or a portion of the polypeptide having the amino acid sequence of SEQ ID NO: 2;
(b) a polypeptide comprising at least amino acids 66-81 of SEQ ID NO: 2;
(c) a polypeptide consisting of amino acids 438-457 of SEQ ID NO: 2; and
(d) a polypeptide consisting of amino acids 111-540 of SEQ ID NO: 13.

9. The method of claim 7, wherein the antibody is a polyclonal antibody.

10. A method of diagnosing cancer in a patient, comprising:
(a) obtaining a biological sample from the patient; and
(b) measuring levels of CLG in said sample with an antibody that binds CLG polypeptide of SEQ ID NO: 2 or SEQ ID NO: 13, wherein levels of CLG in said sample greater than a base line level is indicative of cancer, wherein the cancer is prostate cancer or breast cancer.

11. The method of claim 10, wherein the biological sample is selected from the group consisting of blood, tissue, serum, stool, urine, sputum, cerebrospinal fluid and supernatant from cell lysate.

12. A method for prognosing cancer in an individual having cancer comprising:
(a) obtaining a biological sample from said individual;
(b) measuring CLG amounts to obtain a CLG level in said sample with an antibody that binds CLG polypeptide of SEQ ID NO: 2 or SEQ ID NO: 13;
(c) correlating said CLG level with a baseline level; and
(d) correlating levels of CLG greater than the baseline with an indication of unfavorable prognosis and levels of CLG at the baseline or less with a favorable prognosis, wherein the cancer is prostate cancer or breast cancer.

13. The method of claim 12, wherein the biological sample is selected from the group consisting of blood, tissue, serum, stool, urine, sputum, cerebrospinal fluid and supernatant from cell lysate.

14. A method for determining the metastatic potential of a tumor comprising measuring the level of CLG expression in said tumor with an antibody that binds CLG polypeptide of SEQ ID NO: 2 or SEQ ID NO: 13, wherein levels of CLG in said tumor greater than a baseline level indicates an increased metastatic potential, wherein the tumor is prostate tumor or breast tumor.

15. The method of claim 10, 12 or 14, wherein the level of the CLG protein is measured.

16. The method of claim 15, wherein the method of measuring the level of CLG levels comprises the steps of:
   (a) contacting a sample or preparation thereof with an antibody or antibody fragment which selectively binds CLG of SEQ ID NO: 2 or SEQ ID NO: 13; and
   (b) detecting whether said antibody or said antibody fragment is bound by said sample and thereby measuring the levels of CLG present.

17. The method according to claim 16, wherein said antibody, or said antibody fragment, is detectably labeled.

18. An isolated and purified CLG having the amino acid sequence set forth in SEQ ID NOS: 2, 4 or 13.

19. A purified polypeptide, the amino acid sequence of which comprises residues 1-384 of SEQ ID NO: 2 or 1-331 of SEQ ID NO: 4.

20. A purified polypeptide, the amino acid sequence of which comprises residues 111-540 of SEQ ID NO: 2.

* * * * *